US010717823B2

(12) United States Patent
Kluesener et al.

(10) Patent No.: US 10,717,823 B2
(45) Date of Patent: *Jul. 21, 2020

(54) SILICONE COMPOUNDS

(71) Applicant: The Procter & Gamble Company, Cincinnati, OH (US)

(72) Inventors: Bernard William Kluesener, Harrison, OH (US); Rachel Morgan Clayton Roeder, Mason, OH (US); Mark Robert Sivik, Mason, OH (US); Rajan Keshav Panandiker, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 192 days.

This patent is subject to a terminal disclaimer.

(21) Appl. No.: 15/590,034

(22) Filed: May 9, 2017

(65) Prior Publication Data

US 2017/0327648 A1   Nov. 16, 2017

Related U.S. Application Data

(60) Provisional application No. 62/335,726, filed on May 13, 2016.

(51) Int. Cl.

| | | |
|---|---|---|
| *C11D 3/37* | (2006.01) | |
| *C08G 77/38* | (2006.01) | |
| *C08G 77/388* | (2006.01) | |
| *C08G 77/392* | (2006.01) | |
| *C08L 83/06* | (2006.01) | |
| *C08L 83/08* | (2006.01) | |
| *C08G 77/22* | (2006.01) | |
| *C08G 77/26* | (2006.01) | |
| *C11D 3/50* | (2006.01) | |
| *A61Q 13/00* | (2006.01) | |
| *A61Q 15/00* | (2006.01) | |
| *A61K 8/898* | (2006.01) | |
| *A61Q 5/02* | (2006.01) | |
| *A61K 8/25* | (2006.01) | |

(52) U.S. Cl.
CPC ............... *C08G 77/22* (2013.01); *A61K 8/25* (2013.01); *A61K 8/898* (2013.01); *A61Q 5/02* (2013.01); *A61Q 13/00* (2013.01); *A61Q 15/00* (2013.01); *C08G 77/26* (2013.01); *C08G 77/388* (2013.01); *C08L 83/08* (2013.01); *C11D 3/373* (2013.01); *C11D 3/507* (2013.01)

(58) Field of Classification Search
CPC ....... C11D 3/124; C11D 3/373; C11D 3/3742; C08G 77/38; C08G 77/388; C08G 77/392; C08L 83/06; C08L 83/08
See application file for complete search history.

(56) References Cited

U.S. PATENT DOCUMENTS

| | | |
|---|---|---|
| 4,137,180 A | 1/1979 | Naik et al. |
| 5,296,622 A | 3/1994 | Uphues et al. |
| 5,352,604 A | 10/1994 | Wilson et al. |
| 5,486,303 A | 1/1996 | Capeci et al. |
| 5,489,392 A | 2/1996 | Capeci et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,574,179 A | 11/1996 | Wahl et al. |
| 5,691,297 A | 11/1997 | Nassano et al. |
| 5,879,584 A | 3/1999 | Bianchetti et al. |
| 6,093,562 A | 7/2000 | Bisgard-Frantzen et al. |
| 6,262,287 B1 | 7/2001 | Anderson et al. |
| 7,141,403 B2 | 11/2006 | Outtrup et al. |
| 2007/0021319 A1* | 1/2007 | Kohle .................... A61K 8/898 512/2 |
| 2007/0275866 A1 | 11/2007 | Dykstra |
| 2016/0137674 A1 | 5/2016 | Panandiker et al. |
| 2016/0145534 A1 | 5/2016 | Berthier et al. |
| 2017/0327647 A1 | 11/2017 | Kluesener et al. |

FOREIGN PATENT DOCUMENTS

| | | | |
|---|---|---|---|
| GB | 2 007 703 A | 5/1979 | |
| WO | WO 96/23874 A1 | 8/1996 | |
| WO | WO 96/28497 A1 | 9/1996 | |
| WO | WO 99/46318 * | 9/1999 | ........... C08G 77/388 |
| WO | WO 99/46318 A1 | 9/1999 | |
| WO | WO 00/60060 A2 | 10/2000 | |
| WO | WO 2009/149130 A2 | 12/2009 | |
| WO | WO 2014/202591 * | 12/2014 | ........... C08G 77/392 |

OTHER PUBLICATIONS

U.S. Appl. No. 15/590,033, filed May 9, 2017, Kluesener, et al.
ASTM D3954-94(Reapproved 2010); Standard Test Method for Dropping Point of Waxes.
Perry, Robert J.; "Pro-fragrant" Silicone Delivery Polymers; Delivery System Handbook for Personal Care and Cosmetic Products—Technology, Applications and Formulations; Jan. 1, 2005; pp. 667-682; William Andrew Publishing; XP055390102.
International Search Report; International Application No. PCT/US2017/031631; dated Jul. 25, 2017; 19 pages.

(Continued)

*Primary Examiner* — Brian P Mruk
(74) *Attorney, Agent, or Firm* — Gregory S. Darley-Emerson

(57) ABSTRACT

The present application relates to silicone compounds, compositions, packaged products and displays comprising such silicone compounds, and processes for making and using such compositions, packaged products and displays comprising such compositions. Such compositions have improved deposition and retention properties that may impart improved benefit characteristics to a composition and/or situs yet which changes its hydrophilicity/charge and/or demonstrates cleavage of the functionalized silicone's functionalization when desired.

20 Claims, No Drawings

(56) References Cited

OTHER PUBLICATIONS

International Search Report; International Application No. PCT/US2017/031632; 10 pages. No date given.
Leo, Albert J.; Methods of Calculating Partition Coefficients; Comprehensive Medicinal Chemistry; 1990; p. 295; vol. 4; C. Hansch, P.G. Sammens, J.B. Taylor and C.A. Ramsden, Eds.; Pergamon Press.

* cited by examiner

SILICONE COMPOUNDS

FIELD OF INVENTION

The present application relates to silicone compounds, compositions, packaged products and displays comprising such silicone compounds, and processes for making and using such compositions, packaged products and displays comprising such compositions.

BACKGROUND OF THE INVENTION

Functionalized silicones such as aminosilicones provide numerous benefits including fabric softness, hair conditioning, fabric anti-wrinkle control, shape maintenance, stain control, and color care. Unfortunately, functionalized silicones can reduce the benefits of compositions, such as cleaning compositions, if such compositions are not formulated with the use of functionalized silicones in mind and/or have other use limitations.

Applicants recognized that such formulation challenge is rooted in the charge of functionalized silicones as the degree of charge and degree of functionalization are interrelated and/or the ability of the functionalized portion of the functionalized silicone to cleave from such functionalized silicone. While one can alter the charge of functionalized silicones by reducing the overall functionalization content of the silicone, such alteration can result in negatives such as a loss in the primary benefits of the functionalized silicones. For example, the reduction of the amino functionalization of an aminosilicone can result in a loss in feel and/or benefit delivery effectiveness. Thus, what is needed are functionalized silicones that retain all the primary benefits of a functionalized silicone during use, yet which change their hydrophilicity/charge and/or demonstrates cleavage of the functionalized silicone's functionalization when desired, for example, after use. Applicants provide such a silicone by incorporating a moiety comprising a cleavable bond between the silicone backbone and the desired functionalization.

SUMMARY OF THE INVENTION

The present application relates to silicone compounds, compositions, packaged products and displays comprising such silicone compounds, and processes for making and using such compositions, packaged products and displays comprising such compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" includes, unless otherwise indicated, granular or powder-form all-purpose or "heavy-duty" washing agents, especially cleaning detergents; solid, granular or powder or beads-form fabric freshening or fabric care compositions; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; fabric care composition; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the term "amine" includes, unless otherwise indicated, primary, secondary, tertiary, and quaternary amines.

As used herein, the articles such as "a" and "an" when used in a claim, are understood to mean one or more of what is claimed or described.

As used herein, the terms "include", "includes" and "including" are meant to be synonymous with the phrase "including but not limited to".

As used herein, the term "solid" includes granular, powder, bar and tablet product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Combinations

A. A silicone compound comprising a silicone moiety, a moiety comprising a functional group and a moiety comprising a cleavable bond, said moiety comprising said cleavable bond linking said silicone moiety and said moiety comprising said functional group is disclosed.

B. The silicone compound according to Paragraph A wherein said silicone moiety has the formula:

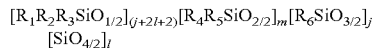

$[R_1R_2R_3SiO_{1/2}]_{(j+2l+2)}[R_4R_5SiO_{2/2}]_m[R_6SiO_{3/2}]_j$
$[SiO_{4/2}]_l$ wherein:
a) j is an integer from 0 to 150, preferably from 0 to 50, more preferably from 0 to 20;
b) m is an integer from 0 to 1500, preferably 1 to 1500, more preferably from 20 to 1000, most preferably from 20 to 400;
c) l is an integer from 0 to 150, preferably from 0 to 150, more preferably from 0 to 50, most preferably from 0 to 20; with the provisio j+m+l equals an integer greater than or equal to 1;
d) each of $R_1$, $R_2$, $R_3$, $R_4$, $R_5$ and $R_6$ moiety is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy, and —$X_t$-A-Y, where in index t is 0 or 1, with the provisio that at least one of the moieties $R_1$ through $R_6$=—$X_t$-A-Y;
(i) each X moiety is independently, a substituted or unsubstituted divalent alkylene radical comprising 1-24 carbon atoms, preferably 1-16 carbon atoms, more preferably 1-12 carbon atoms, most preferably 2-12 carbon atoms;
(ii) each A moiety is independently selected from the group consisting of

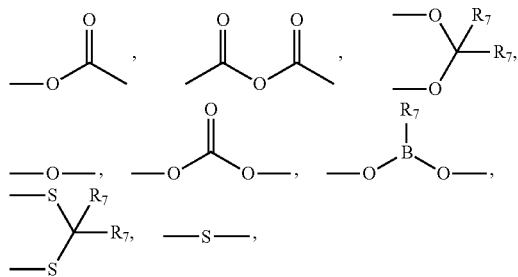

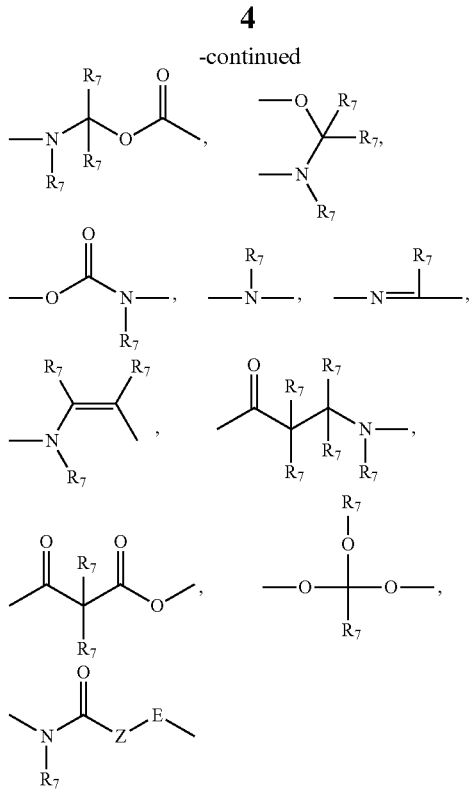

E=electron withdrawing group, preferably E is selected from the group consisting of O, S, an aryl moiety and an alkene moiety,

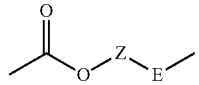

E=electron withdrawing group, preferably E is selected from the group consisting of O, S, a halide, an aryl moiety and an alkene moiety;

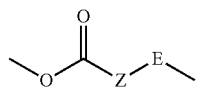

E=electron withdrawing group, preferably E is selected from the group consisting of O, S, an aryl moiety and an alkene moiety;

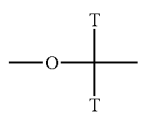

wherein each T is selected from an electron withdrawing group E or $R_7$, with the proviso that at least one T is E; preferably E is selected from the group consisting of O, S, an aryl moiety and an alkene moiety; each $R_7$ moiety for each A moiety is independently selected from the group consisting of H, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl; and each Z for each A moiety is independently selected from the group consisting of:

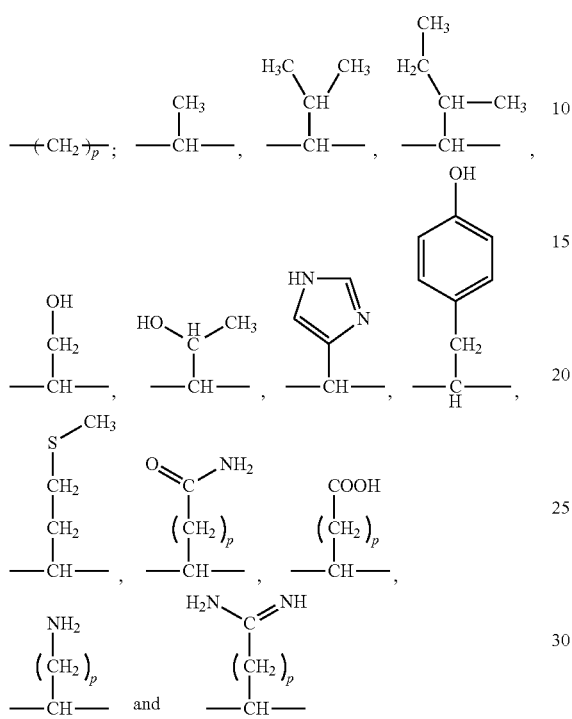

where p is an integer from 1-32, preferably p is an integer form 1-10, more preferably p is an integer from 2 to 8, most preferably p in an integer from 2 to 4;

(ii) each Y moiety is independently selected from the group consisting of a $C_1$-$C_{32}$ alkyl, a $C_5$-$C_{32}$ aryl, and a $C_6$-$C_{32}$ alkylaryl comprising at least one substituent selected from the group consisting of an ether moiety, an alkene moiety, an alkyne moiety, an aldehyde moiety, a ketone moiety, an ester moiety, a carbonate moiety, an amide moiety, a nitrile moiety, a peroxide moiety, an acetal moiety, a hemiacetal moiety, a hemiketal moiety, a ketal moiety, an orthoester moiety, orthocarbonate ester, an imine moiety, an imide moiety, an azide moiety, an azo moiety, a cyanate moiety, a nitrate moiety, a nitrite moiety, a nitro moiety, a nitroso moiety, an oxime, a sulfide moiety, a disulfide moiety, a sulfoxide moiety, a sulfone moiety, a sulfinic acid moiety, a sulfonic acid moiety, a thiocyanate moiety, a thione moiety, a thial moiety, a phosphine moiety, a phosphonic acid moiety, a phosphate moiety, a phosphodiester moiety, a boronic acid moiety, a boronic ester moiety, a borinic acid moiety, a borinic ester moiety, an amino moiety, an epoxy moiety, an alkoxy moiety, a hydroxy moiety, a thiol moiety, a halide moiety, an oxyalkylene moiety, an anhydride moiety, a carboxy moiety, a silane moiety, a siloxane moiety and a quaternary ammonium moiety; preferably said at least one substituent is selected from the group consisting of an amino moiety, an epoxy moiety, an alkoxy moiety, a hydroxy moiety, a thiol moiety, a halide moiety, an oxyalkylene moiety, an anhydride moiety, a carboxy moiety and a quaternary ammonium moiety; more preferably said at least one substituent is selected from the group consisting of an amino moiety, a hydroxy moiety, a thiol moiety, a carboxy moiety and a quaternary ammonium moiety.

C. A silicone compound according to Paragraphs A or B wherein each A moiety is independently selected from the group consisting of:

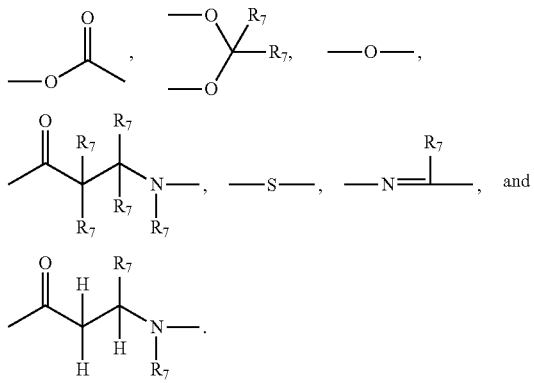

D. A silicone compound according to Paragraphs A or B wherein each Y moiety is independently selected from the group consisting of

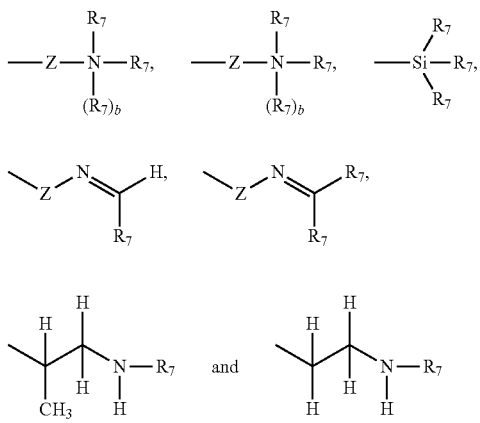

wherein b is 0 or 1 with the proviso that when b=1, the positive charge on the nitrogen is balanced by a suitable anion, preferably said anion is selected from the group consisting of methyl sulfate, chloride and bromide and each Z for each A moiety is independently selected from the group consisting of:

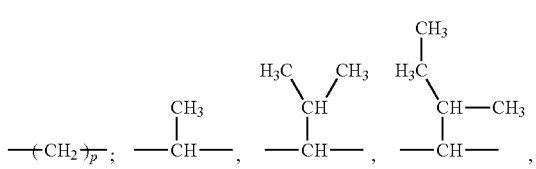

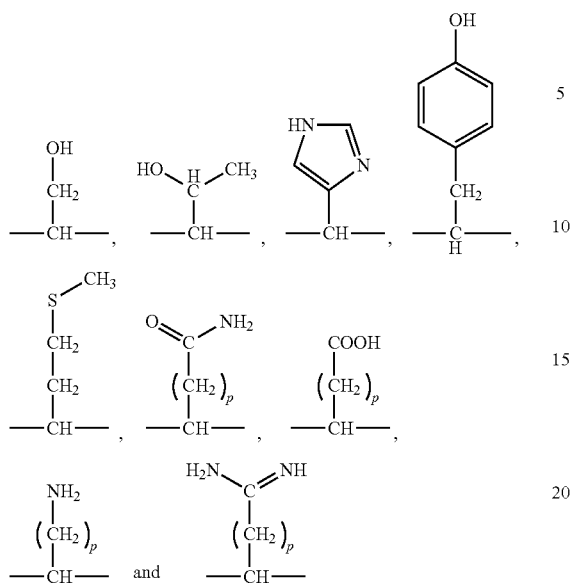

where p is an integer from 1-32, preferably p is an integer form 1-10, more preferably p is an integer from 2 to 8, most preferably p in an integer from 2 to 4.

E. A silicone compound according to Paragraphs A through D wherein each A-Y moiety is independently selected from the group consisting of:

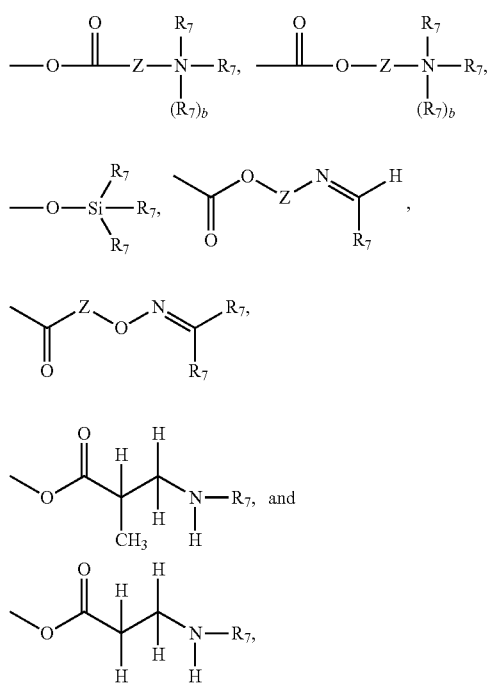

wherein b is 0 or 1, with the proviso that if b=1 then, the positive charge on the nitrogen is balanced by a suitable anion, preferably said anion is selected from the group consisting of methyl sulfate, chloride and bromide and each Z for each A moiety is independently selected from the group consisting of:

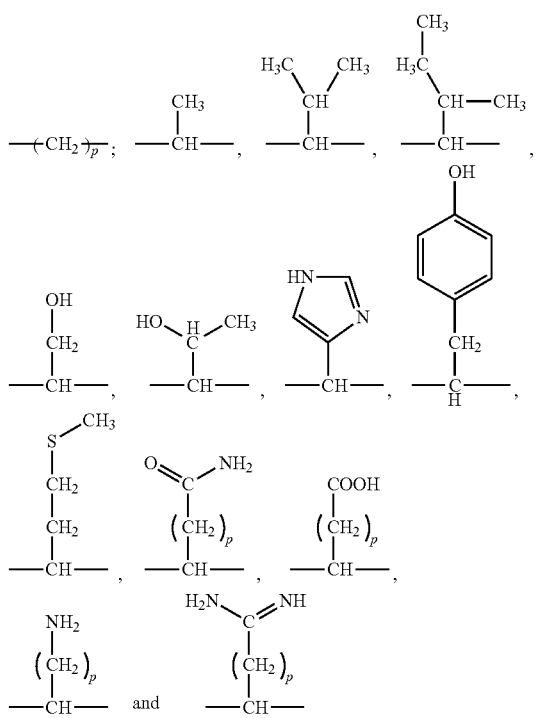

where p is an integer from 1-32, preferably p is an integer form 1-10, more preferably p is an integer from 2 to 8, most preferably p in an integer from 2 to 4.

F. A consumer product composition comprising:
  a.) from about 0.001% to about 10%, preferably from about 0.05% to about 7%, more preferably from about 0.1% to about 5%, most preferably from about 1% to about 3% of a silicone compound according to Paragraphs A through E; and
  b.) a consumer product ingredient.

G. A consumer product according to Paragraph F, said consumer product being a cleaning and/or treatment composition.

H. A cleaning and/or treatment composition according to Paragraphs F or G, comprising a consumer product ingredient selected from the group consisting of surfactants, color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume, an additional perfume delivery system, structure elasticizing agents, thickeners/structurants, fabric softeners, carriers, hydrotropes, oligoamines, processing aids, hueing agents, pigments and mixtures thereof.

I. A consumer product comprising a silicone compound according to Paragraphs A through E and packaging, preferably said packaging comprises a silicone compound according to Paragraphs A through E that is attached or adhered to said packaging. Such packing may take any form including wrapping, or a container. Silicone compounds according to Paragraphs A through E may be adhered or attached to the exterior and/or the interior surface of such packaging. Said packaging may comprise a container comprising a cap and said silicone compounds according to Paragraphs A through E may be adhered or attached to the exterior or interior surface of said cap.

J. A display comprising a silicone compound according to Paragraphs A through E and a display material, said silicone compound being attached or adhered to said display material.

K. The silicone compound disclosed in Paragraphs A through E herein may be incorporated into solid particles, particularly polymeric based particles. Examples of such polymeric particles may include particles comprising polyethylene glycol, starches and polysaccharides, polyvinyl alcohol, celluloses. Such particles may additionally comprise additional components such as other benefit agents, inorganic fillers such as carbonate, silicate, clay, metal oxides. Particularly useful particles include particles based on polyethylene glycol.

The consumer products of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; 5,486,303 all of which are incorporated herein by reference.

Method of Use and Treated Situs

Compositions containing the silicone compound disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

A method of treating and/or cleaning a situs, said method comprising
a.) optionally washing and/or rinsing said situs;
b.) contacting said situs with a silicone compound according to Paragraphs A through E and/or a consumer product according to Paragraphs F through I; and
c.) optionally washing and/or rinsing said situs.

A situs treated with a silicone compound according to Paragraphs A through E and/or a consumer product according to Paragraphs F through I is disclosed.

Adjunct Materials

While not essential for each consumer product embodiment of the present invention, the non-limiting list of adjuncts illustrated hereinafter are suitable for use in the instant consumer products and may be desirably incorporated in certain embodiments of the invention, for example to assist or enhance performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the operation for which it is to be used. Suitable adjunct materials include, but are not limited to surfactants, color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume and perfume delivery systems, structure elasticizing agents, thickeners/structurants, fabric softeners, carriers, hydrotropes, oligoamines, processing aids, hueing agents, and/or pigments.

As stated, the adjunct ingredients are not essential for each consumer product embodiment of the present invention. Thus, certain embodiments of Applicants' compositions do not contain one or more of the following adjuncts materials: surfactants, color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume and perfume delivery systems, structure elasticizing agents, thickeners/structurants, fabric softeners, carriers, hydrotropes, oligoamines, processing aids, hueing agents, and/or pigments. However, when one or more adjuncts is present, such one or more adjuncts may be present as detailed below.

Suitable Fabric Softening Actives

The fluid fabric enhancer compositions disclosed herein comprise a fabric softening active ("FSA"). Suitable fabric softening actives, include, but are not limited to, materials selected from the group consisting of quaternary ammonium compounds, amines, fatty esters, sucrose esters, silicones, dispersible polyolefins, clays, polysaccharides, fatty acids, softening oils, polymer latexes and mixtures thereof.

Non-limiting examples of water insoluble fabric care benefit agents include dispersible polyethylene and polymer latexes. These agents can be in the form of emulsions, latexes, dispersions, suspensions, and the like. In one aspect, they are in the form of an emulsion and/or a latex. Dispersible polyethylenes and polymer latexes can have a wide range of particle size diameters ($\chi_{50}$) including but not limited to from about 1 nm to about 100 µm; alternatively from about 10 nm to about 10 µm. As such, the particle sizes of dispersible polyethylenes and polymer latexes are generally, but without limitation, smaller than silicones or other fatty oils. Generally, any surfactant suitable for making polymer emulsions or emulsion polymerizations of polymer latexes can be used to make the water insoluble fabric care benefit agents of the present invention. Suitable surfactants consist of emulsifiers for polymer emulsions and latexes, dispersing agents for polymer dispersions and suspension agents for polymer suspensions. Suitable surfactants include anionic, cationic, and nonionic surfactants, or combinations thereof. In one aspect, such surfactants are nonionic and/or anionic surfactants. In one aspect, the ratio of surfactant to polymer in the water insoluble fabric care benefit agent is about 1:100 to about 1:2; alternatively from about 1:50 to about 1:5, respectively. Suitable water insoluble fabric care benefit agents include but are not limited to the examples described below.

Quat—

Suitable quats include but are not limited to, materials selected from the group consisting of ester quats, amide quats, imidazoline quats, alkyl quats, amdioester quats and mixtures thereof. Suitable ester quats include but are not limited to, materials selected from the group consisting of monoester quats, diester quats, triester quats and mixtures thereof. In one aspect, a suitable ester quat is bis-(2-hydroxypropyl)-dimethylammonium methylsulphate fatty acid ester having a molar ratio of fatty acid moieties to amine moieties of from 1.85 to 1.99, an average chain length of the fatty acid moieties of from 16 to 18 carbon atoms and an iodine value of the fatty acid moieties, calculated for the free fatty acid, of from 0.5 to 140, or from 0.5 to 60, from 15 to 50 or from 15 to 25. In one aspect, the cis-trans-ratio of double bonds of unsaturated fatty acid moieties of the bis (2 hydroxypropyl)-dimethylammonium methylsulphate fatty acid ester is from 55:45 to 75:25, respectively. Suitable amide quats include but are not limited to, materials selected from the group consisting of monoamide quats, diamide quats and mixtures thereof. Suitable alkyl quats include but are not limited to, materials selected from the group consisting of mono alkyl quats, dialkyl quats, trialkyl quats, tetraalkyl quats and mixtures thereof.

Amines—

Suitable amines include but are not limited to, materials selected from the group consisting of amidoesteramines, amidoamines, imidazoline amines, alkyl amines, amdioester amines and mixtures thereof. Suitable ester amines include but are not limited to, materials selected from the group consisting of monoester amines, diester amines, triester amines and mixtures thereof. Suitable amido quats include but are not limited to, materials selected from the group consisting of monoamido amines, diamido amines and mixtures thereof. Suitable alkyl amines include but are not limited to, materials selected from the group consisting of mono alkylamines, dialkyl amines quats, trialkyl amines, and mixtures thereof.

In one embodiment, the fabric softening active is a quaternary ammonium compound suitable for softening fabric in a rinse step. In one embodiment, the fabric softening active is formed from a compound of a fatty acid and an aminoalcohol obtaining mixtures of mono-, di-, and, in one embodiment, tri-ester compounds. In another embodiment, the fabric softening active comprises one or more softener quaternary ammonium compounds such, but not limited to, as a monoalkyquaternary ammonium compound, dialkylquaternary ammonium compound, a diamido quaternary compound, a diester quaternary ammonium compound, or a combination thereof.

In one aspect, the fabric softening active comprises a diester quaternary ammonium or protonated diester ammonium (hereinafter "DQA") compound composition. In certain embodiments of the present invention, the DQA compound compositions also encompass diamido fabric softening actives and fabric softening actives with mixed amido and ester linkages as well as the aforementioned diester linkages, all herein referred to as DQA. In one aspect, said fabric softening active may comprise, as the principal active, compounds of the following formula:

{R4-m-N+-[X—Y—R1]m}X— (1)

wherein each R comprises either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X is independently $(CH_2)n$, $CH_2$—$CH(CH_3)$— or CH—$(CH_3)$—$CH_2$—; each Y may comprise —O—(O)C—, —C(O)—O—, —NR—C(O)—, or —C(O)—NR—; each m is 2 or 3; each n is from 1 to about 4, in one aspect 2; the sum of carbons in each R1, plus one when Y is —O—(O)C— or —NR—C(O)—, may be $C_{12}$-$C_{22}$, or $C_{14}$-$C_{20}$, with each R1 being a hydrocarbyl, or substituted hydrocarbyl group; and X— may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

In another aspect, the fabric softening active may comprise the general formula:

[R3N+CH2CH(YR1)(CH2YR1)]X— wherein each Y, R, R1, and X— have the same meanings as before. Such compounds include those having the formula:

  (2)

wherein each R may comprise a methyl or ethyl group. In one aspect, each R1 may comprise a $C_{15}$ to $C_{19}$ group. As used herein, when the diester is specified, it can include the monoester that is present.

These types of agents and general methods of making them are disclosed in U.S. Pat. No. 4,137,180. An example of a suitable DEQA (2) is the "propyl" ester quaternary ammonium fabric softener active comprising the formula 1,2-di(acyloxy)-3-trimethylammoniopropane chloride. A third type of useful fabric softening active has the formula:

[R4-m-N+-R1m]X— (3)

wherein each R, R1, m and X— have the same meanings as before.

In a further aspect, the fabric softening active may comprise the formula:

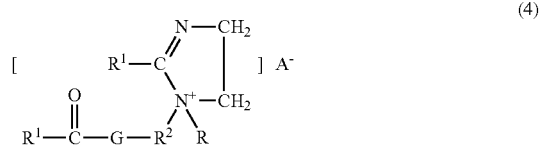

(4)

wherein each R, R1, and A- have the definitions given above; R2 may comprise a $C_{1-6}$ alkylene group, in one aspect an ethylene group; and G may comprise an oxygen atom or an —NR— group;

In a yet further aspect, the fabric softening active may comprise the formula:

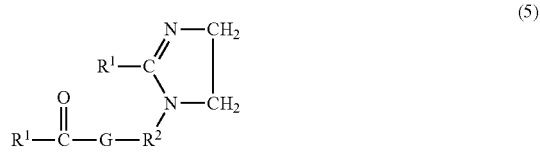

(5)

wherein R1, R2 and G are defined as above.

In a further aspect, the fabric softening active may comprise condensation compounds of fatty acids with dialkylenetriamines in, e.g., a molecular ratio of about 2:1, said compounds containing compounds of the formula:

R1-C(O)—NH—R2-NH—R3-NH—C(O)—R1 (6)

wherein R1, R2 are defined as above, and R3 may comprise a C1-6 alkylene group, in one aspect, an ethylene group and wherein the compounds may optionally be quaternized by the additional of an alkylating agent such as dimethyl sulfate. Such quaternized compounds are described in additional detail in U.S. Pat. No. 5,296,622.

In a yet further aspect, the fabric softening active may comprise the formula:

[R1-C(O)—NR—R2-N(R)2-R3-NR—C(O)—R1]+A- (7)

wherein R, R1, R2, R3 and A- are defined as above;

In a yet further aspect, the fabric softening active may comprise compounds of fatty acid with hydroxyalkylalkylenediamines in a molecular ratio of about 2:1, said compounds containing compounds of the formula:

R1-C(O)—NH—R2-N(R3OH)—C(O)—R1 (8)

wherein R1, R2 and R3 are defined as above;

In a yet further aspect, the fabric softening active may comprise the formula:

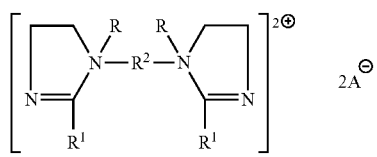
(9)

wherein R, R1, R2, and A- are defined as above.

In yet a further aspect, the fabric softening active may comprise the formula:

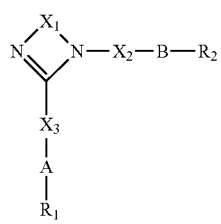
(10)

wherein;
X$_1$ is a C$_{2-3}$ alkyl group, in one aspect, an ethyl group;
X$_2$ and X$_3$ are independently C$_{1-6}$ linear or branched alkyl or alkenyl groups, in one aspect, methyl, ethyl or isopropyl groups;
R$_1$ and R$_2$ are independently C$_{8-22}$ linear or branched alkyl or alkenyl groups; characterized in that;
A and B are independently selected from the group comprising —O—(C=O)—, —(C=O)—O—, or mixtures thereof, in one aspect, —O—(C=O)—

Non-limiting examples of fabric softening actives comprising formula (1) are N, N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate.

Non-limiting examples of fabric softening actives comprising formula (2) is 1,2 di (stearoyl-oxy) 3 trimethyl ammoniumpropane chloride.

Non-limiting examples of fabric softening actives comprising formula (3) include dialkylenedimethylammonium salts such as dicanoladimethylammonium chloride, di(hard)tallowdimethylammonium chloride dicanoladimethylammonium methylsulfate, and mixtures thereof. An example of commercially available dialkylenedimethylammonium salts usable in the present invention is dioleyldimethylammonium chloride available from Witco Corporation under the trade name Adogen® 472 and dihardtallow dimethylammonium chloride available from Akzo Nobel Arquad 2HT75.

A non-limiting example of fabric softening actives comprising formula (4) is 1-methyl-1-stearoylamidoethyl-2-stearoylimidazolinium methylsulfate wherein R1 is an acyclic aliphatic C15-C17 hydrocarbon group, R2 is an ethylene group, G is a NH group, R5 is a methyl group and A- is a methyl sulfate anion, available commercially from the Witco Corporation under the trade name Varisoft®.

A non-limiting example of fabric softening actives comprising formula (5) is 1-tallowylamidoethyl-2-tallowylimidazoline wherein R1 is an acyclic aliphatic C15-C17 hydrocarbon group, R2 is an ethylene group, and G is a NH group.

A non-limiting example of a fabric softening active comprising formula (6) is the compounds of fatty acids with diethylenetriamine in a molecular ratio of about 2:1, said compound mixture containing N,N"-dialkyldiethylenetriamine with the formula:

R1-C(O)—NH—CH2CH2-NH—CH2CH2-NH—C(O)—R1 wherein R1 is an alkyl group of a commercially available fatty acid derived from a vegetable or animal source, such as Emersol® 223LL or Emersol® 7021, available from Henkel Corporation, and R2 and R3 are divalent ethylene groups.

In one aspect, said fatty acid may be obtained, in whole or in part, from a renewable source, via extraction from plant material, fermentation from plant material, and/or obtained via genetically modified organisms such as algae or yeast.

A non-limiting example of Compound (7) is a di-fatty amidoamine based softener having the formula:

[R1-C(O)—NH—CH2CH2-N(CH3)(CH2CH2OH)—CH2CH2-NH—C(O)—R1]+CH3SO4- wherein R1 is an alkyl group. An example of such compound is that commercially available from the Witco Corporation e.g. under the trade name Varisoft® 222LT.

An example of a fabric softening active comprising formula (8) is the compounds of fatty acids with N-2-hydroxyethylethylenediamine in a molecular ratio of about 2:1, said compound mixture containing a compound of the formula:

R1-C(O)—NH—CH2CH2-N(CH2CH2OH)—C(O)—R1 wherein R1-C(O) is an alkyl group of a commercially available fatty acid derived from a vegetable or animal source, such as Emersol® 223LL or Emersol® 7021, available from Henkel Corporation.

An example of a fabric softening active comprising formula (9) is the diquaternary compound having the formula:

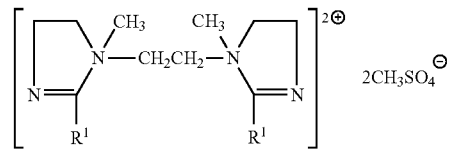

wherein R1 is derived from fatty acid. Such compound is available from Witco Company.

A non-limiting example of a fabric softening active comprising formula (10) is a dialkyl imidazoline diester compound, where the compound is the compound of N-(2-hydroxyethyl)-1,2-ethylenediamine or N-(2- hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid or a mixture of the above.

It will be understood that combinations of softener actives disclosed above are suitable for use in this invention.

Anion A

In the cationic nitrogenous salts herein, the anion A-, which comprises any softener compatible anion, provides electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, fatty acid anions and the like. In one aspect, the anion A may comprise chloride or methylsulfate. The anion, in some aspects, may carry a double charge. In this aspect, A-represents half a group.

In one embodiment, the fabric softening agent is chosen from at least one of the following: said fabric softener active material comprises a fabric softener active selected from the group consisting of bis-(2-hydroxypropyl)-dimethylammonium methylsulphate fatty acid ester, 1,2-di(acyloxy)-3-trimethylammoniopropane chloride, N, N-bis(stearoyl-oxy-ethyl)-N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)-N-methyl ammonium methylsulfate, N,N-bis-(stearoyl-2-hydroxypropyl)-N,N-dimethylammonium methylsulphate, N,N-bis-(tallowoyl-2-hydroxypropyl)-N,N-dimethylammonium methylsulphate, N,N-bis-(palmitoyl-2-hydroxypropyl)-N,N-dimethylammonium methylsulphate, N,N-bis-(stearoyl-2-hydroxypropyl)-N,N-dimethylammonium chloride, 1,2 di(stearoyl-oxy) 3 trimethyl ammoniumpropane chloride, dicanoladimethylammonium chloride, di(hard)tallowdimethylammonium chloride dicanoladimethylammonium methylsulfate, 1-methyl-1-stearoylamidoethyl-2-stearoylimidazolinium methylsulfate, 1-tallowylamidoethyl-2-tallowylimidazoline, dipalmethyl hydroxyethylammonium methosulfate and mixtures thereof.

Polysaccharides

One aspect of the invention provides a fabric enhancer composition comprising a cationic starch as a fabric softening active. In one embodiment, the fabric care compositions of the present invention generally comprise cationic starch at a level of from about 0.1% to about 7%, alternatively from about 0.1% to about 5%, alternatively from about 0.3% to about 3%, and alternatively from about 0.5% to about 2.0%, by weight of the composition. Suitable cationic starches for use in the present compositions are commercially-available from Cerestar under the trade name C*BOND® and from National Starch and Chemical Company under the trade name CATO® 2A.

Sucrose Esters

Nonionic fabric care benefit agents can comprise sucrose esters, and are typically derived from sucrose and fatty acids. Sucrose ester is composed of a sucrose moiety having one or more of its hydroxyl groups esterified.

Sucrose is a disaccharide having the following formula:

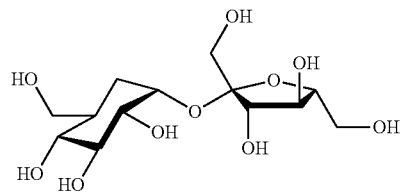

Alternatively, the sucrose molecule can be represented by the formula: $M(OH)_8$, wherein M is the disaccharide backbone and there are total of 8 hydroxyl groups in the molecule.

Thus, sucrose esters can be represented by the following formula:

$$M(OH)_{8-x}(OC(O)R^1)_x$$

wherein x is the number of hydroxyl groups that are esterified, whereas (8-x) is the hydroxyl groups that remain unchanged; x is an integer selected from 1 to 8, alternatively from 2 to 8, alternatively from 3 to 8, or from 4 to 8; and $R^1$ moieties are independently selected from $C_1$-$C_{22}$ alkyl or $C_1$-$C_{30}$ alkoxy, linear or branched, cyclic or acyclic, saturated or unsaturated, substituted or unsubstituted.

In one embodiment, the $R^1$ moieties comprise linear alkyl or alkoxy moieties having independently selected and varying chain length. For example, $R^1$ may comprise a mixture of linear alkyl or alkoxy moieties wherein greater than about 20% of the linear chains are $C_{18}$, alternatively greater than about 50% of the linear chains are $C_{18}$, alternatively greater than about 80% of the linear chains are $C_{18}$.

In another embodiment, the $R^1$ moieties comprise a mixture of saturate and unsaturated alkyl or alkoxy moieties; the degree of unsaturation can be measured by "Iodine Value" (hereinafter referred as "IV", as measured by the standard AOCS method). The IV of the sucrose esters suitable for use herein ranges from about 1 to about 150, or from about 2 to about 100, or from about 5 to about 85. The $R^1$ moieties may be hydrogenated to reduce the degree of unsaturation.

In the case where a higher IV is preferred, such as from about 40 to about 95, then oleic acid and fatty acids derived from soybean oil and canola oil are the starting materials.

In a further embodiment, the unsaturated $R^1$ moieties may comprise a mixture of "cis" and "trans" forms about the unsaturated sites. The "cis"/"trans" ratios may range from about 1:1 to about 50:1, or from about 2:1 to about 40:1, or from about 3:1 to about 30:1, or from about 4:1 to about 20:1.

Dispersible Polyolefins

Generally, all dispersible polyolefins that provide fabric care benefits can be used as water insoluble fabric care benefit agents in the present invention. The polyolefins can be in the format of waxes, emulsions, dispersions or suspensions. Non-limiting examples are discussed below. In one embodiment, the polyolefin is chosen from a polyethylene, polypropylene, or a combination thereof. The polyolefin may be at least partially modified to contain various functional groups, such as carboxyl, alkylamide, sulfonic acid or amide groups. In another embodiment, the polyolefin is at least partially carboxyl modified or, in other words, oxidized.

For ease of formulation, the dispersible polyolefin may be introduced as a suspension or an emulsion of polyolefin dispersed by use of an emulsifying agent. The polyolefin suspension or emulsion may comprise from about 1% to about 60%, alternatively from about 10% to about 55%, alternatively from about 20% to about 50% by weight of polyolefin. The polyolefin may have a wax dropping point (see ASTM D3954-94, volume 15.04—"Standard Test Method for Dropping Point of Waxes") from about 20° to about 170° C., alternatively from about 50° to about 140° C. Suitable polyethylene waxes are available commercially from suppliers including but not limited to Honeywell (A-C polyethylene), Clariant (Velustrol® emulsion), and BASF) (LUWAX®).

When an emulsion is employed with the dispersible polyolefin, the emulsifier may be any suitable emulsification agent. Non-limiting examples include an anionic, cationic, nonionic surfactant, or a combination thereof. However, almost any suitable surfactant or suspending agent may be employed as the emulsification agent. The dispersible polyolefin is dispersed by use of an emulsification agent in a ratio to polyolefin wax of about 1:100 to about 1:2, alternatively from about 1:50 to about 1:5, respectively.

Polymer Latexes

Polymer latex is made by an emulsion polymerization which includes one or more monomers, one or more emulsifiers, an initiator, and other components familiar to those of ordinary skill in the art. Generally, all polymer latexes that provide fabric care benefits can be used as water insoluble fabric care benefit agents of the present invention. Additional non-limiting examples include the monomers used in producing polymer latexes such as: (1) 100% or pure butylacrylate; (2) butylacrylate and butadiene mixtures with at least 20% (weight monomer ratio) of butylacrylate; (3) butylacrylate and less than 20% (weight monomer ratio) of other monomers excluding butadiene; (4) alkylacrylate with an alkyl carbon chain at or greater than $C_6$; (5) alkylacrylate with an alkyl carbon chain at or greater than $C_6$ and less than 50% (weight monomer ratio) of other monomers; (6) a third monomer (less than 20% weight monomer ratio) added into an aforementioned monomer systems; and (7) combinations thereof.

Polymer latexes that are suitable fabric care benefit agents in the present invention may include those having a glass transition temperature of from about −120° C. to about 120° C., alternatively from about −80° C. to about 60° C. Suitable emulsifiers include anionic, cationic, nonionic and ampoteric surfactants. Suitable initiators include initiators that are suitable for emulsion polymerization of polymer latexes. The particle size diameter ($\chi_{50}$) of the polymer latexes can be from about 1 nm to about 10 μm, alternatively from about 10 nm to about 1 μm, or even from about 10 nm to about 20 nm.

Fatty Acid

One aspect of the invention provides a fabric softening composition comprising a fatty acid, such as a free fatty acid. The term "fatty acid" is used herein in the broadest sense to include unprotonated or protonated forms of a fatty acid; and includes fatty acid that is bound or unbound to another chemical moiety as well as the various combinations of these species of fatty acid. One skilled in the art will readily appreciate that the pH of an aqueous composition will dictate, in part, whether a fatty acid is protonated or unprotonated. In another embodiment, the fatty acid is in its unprotonated, or salt form, together with a counter ion, such as, but not limited to, calcium, magnesium, sodium, potassium and the like. The term "free fatty acid" means a fatty acid that is not bound to another chemical moiety (covalently or otherwise) to another chemical moiety.

In one embodiment, the fatty acid may include those containing from about 12 to about 25, from about 13 to about 22, or even from about 16 to about 20, total carbon atoms, with the fatty moiety containing from about 10 to about 22, from about 12 to about 18, or even from about 14 (mid-cut) to about 18 carbon atoms.

The fatty acids of the present invention may be derived from (1) an animal fat, and/or a partially hydrogenated animal fat, such as beef tallow, lard, etc.; (2) a vegetable oil, and/or a partially hydrogenated vegetable oil such as canola oil, safflower oil, peanut oil, sunflower oil, sesame seed oil, rapeseed oil, cottonseed oil, corn oil, soybean oil, tall oil, rice bran oil, palm oil, palm kernel oil, coconut oil, other tropical palm oils, linseed oil, tung oil, etc.; (3) processed and/or bodied oils, such as linseed oil or tung oil via thermal, pressure, alkali-isomerization and catalytic treatments; (4) a mixture thereof, to yield saturated (e.g. stearic acid), unsaturated (e.g. oleic acid), polyunsaturated (linoleic acid), branched (e.g. isostearic acid) or cyclic (e.g. saturated or unsaturated α-disubstituted cyclopentyl or cyclohexyl derivatives of polyunsaturated acids) fatty acids.

Mixtures of fatty acids from different fat sources can be used.

In one aspect, at least a majority of the fatty acid that is present in the fabric softening composition of the present invention is unsaturated, e.g., from about 40% to 100%, from about 55% to about 99%, or even from about 60% to about 98%, by weight of the total weight of the fatty acid present in the composition, although fully saturated and partially saturated fatty acids can be used. As such, the total level of polyunsaturated fatty acids (TPU) of the total fatty acid of the inventive composition may be from about 0% to about 75% by weight of the total weight of the fatty acid present in the composition.

The cis/trans ratio for the unsaturated fatty acids may be important, with the cis/trans ratio (of the C18:1 material) being from at least about 1:1, at least about 3:1, from about 4:1 or even from about 9:1 or higher.

Branched fatty acids such as isostearic acid are also suitable since they may be more stable with respect to oxidation and the resulting degradation of color and odor quality.

The Iodine Value or "IV" measures the degree of unsaturation in the fatty acid. In one embodiment of the invention, the fatty acid has an IV from about 10 to about 140, from about 15 to about 100 or even from about 15 to about 60.

Another class of fatty ester fabric care actives is softening oils, which include but are not limited to, vegetable oils (such as soybean, sunflower, and canola), hydrocarbon based oils (natural and synthetic petroleum lubricants, in one aspect polyolefins, isoparaffins, and cyclic paraffins), triolein, fatty esters, fatty alcohols, fatty amines, fatty amides, and fatty ester amines Oils can be combined with fatty acid softening agents, clays, and silicones.

Clays

In one embodiment of the invention, the fabric care composition may comprise a clay as a fabric care active. In one embodiment clay can be a softener or co-softeners with another softening active, for example, silicone. Suitable clays include those materials classified geologically smectites.

Silicone

In one embodiment, the fabric softening composition comprises a silicone. Suitable levels of silicone may comprise from about 0.1% to about 70%, alternatively from about 0.3% to about 40%, alternatively from about 0.5% to about 30%, alternatively from about 1% to about 20% by weight of the composition. Useful silicones can be any silicone comprising compound. In one embodiment, the silicone polymer is selected from the group consisting of cyclic silicones, polydimethylsiloxanes, aminosilicones, cationic silicones, silicone polyethers, silicone resins, silicone urethanes, and mixtures thereof. In one embodiment, the silicone is a polydialkylsilicone, alternatively a polydimethyl silicone (polydimethyl siloxane or "PDMS"), or a derivative thereof. In another embodiment, the silicone is chosen from an aminofunctional silicone, amino-polyether silicone, alkyloxylated silicone, cationic silicone, ethoxylated silicone, propoxylated silicone, ethoxylated/propoxylated silicone, quaternary silicone, or combinations thereof.

In another embodiment, the silicone may be chosen from a random or blocky organosilicone polymer having the following formula:

[R$_1$R$_2$R$_3$SiO$_{1/2}$]$_{(j+2)}$[(R$_4$Si(X—Z)O$_{2/2}$]$_k$[R$_4$R$_4$SiO$_{2/2}$]$_m$ [R$_4$SiO$_{3/2}$]$_j$ wherein:

j is an integer from 0 to about 98; in one aspect j is an integer from 0 to about 48; in one aspect, j is 0;

k is an integer from 0 to about 200, in one aspect k is an integer from 0 to about 50; when k=0, at least one of R$_1$, R$_2$ or R$_3$ is —X—Z;

m is an integer from 4 to about 5,000; in one aspect m is an integer from about 10 to about 4,000; in another aspect m is an integer from about 50 to about 2,000;

R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy and X—Z;

each R$_4$ is independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy and C$_1$-C$_{32}$ substituted alkoxy;

each X in said alkyl siloxane polymer comprises a substituted or unsubstituted divalent alkylene radical comprising 2-12 carbon atoms, in one aspect each divalent alkylene radical is independently selected from the group consisting of —(CH$_2$)$_s$— wherein s is an integer from about 2 to about 8, from about 2 to about 4; in one aspect, each X in said alkyl siloxane polymer comprises a substituted divalent alkylene radical selected from the group consisting of: —CH$_2$—CH(OH)—CH$_2$—; —CH$_2$—CH$_2$—CH(OH)—; and

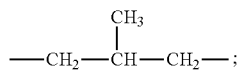

each Z is selected independently from the group consisting of

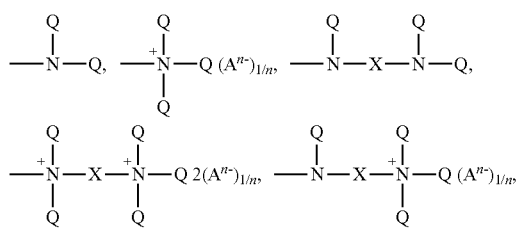

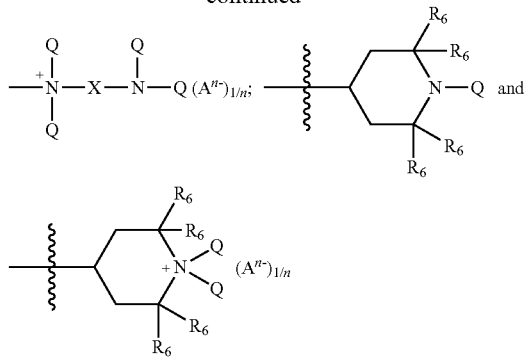

with the proviso that when Z is a quat, Q cannot be an amide, imine, or urea moiety and if Q is an amide, imine, or urea moiety, then any additional Q bonded to the same nitrogen as said amide, imine, or urea moiety must be H or a C$_1$-C$_6$ alkyl, in one aspect, said additional Q is H; for Z A$^{n-}$ is a suitable charge balancing anion. In one aspect A$^{n-}$ is selected from the group consisting of Cl$^-$, Br$^-$, I$^-$, methylsulfate, toluene sulfonate, carboxylate and phosphate; and at least one Q in said organosilicone is independently selected from

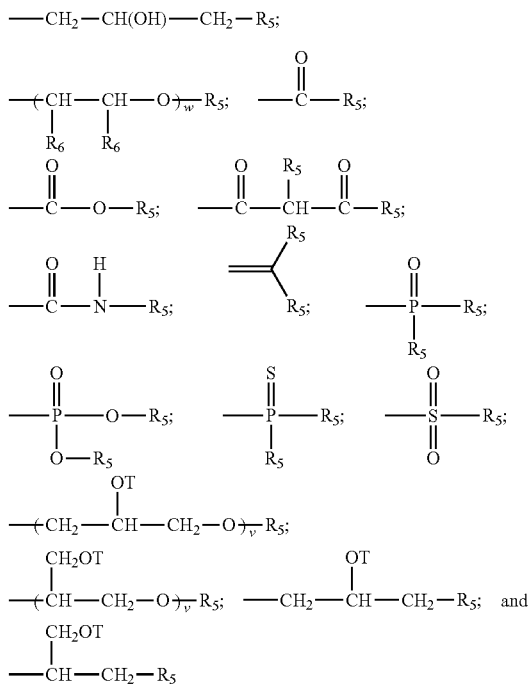

each additional Q in said organosilicone is independently selected from the group comprising of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, —CH$_2$—CH(OH)—CH$_2$—R$_5$;

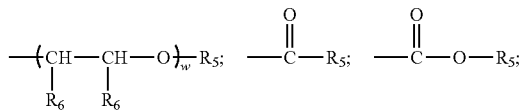

-continued

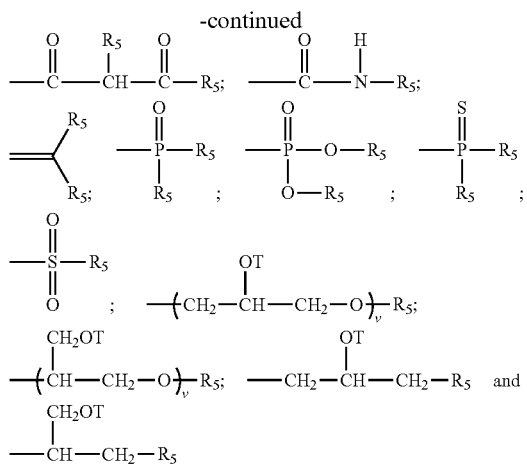

wherein each R$_5$ is independently selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, —(CHR$_6$—CHR$_6$—O—)$_w$-L and a siloxyl residue;
each R$_6$ is independently selected from H, C$_1$-C$_{18}$ alkyl
each L is independently selected from —C(O)—R$_7$ or R$_7$;
w is an integer from 0 to about 500, in one aspect w is an integer from about 1 to about 200; in one aspect w is an integer from about 1 to about 50;
each R$_7$ is selected independently from the group consisting of H; C$_1$-C$_{32}$ alkyl; C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl; C$_6$-C$_{32}$ substituted alkylaryl and a siloxyl residue;
each T is independently selected from H, and

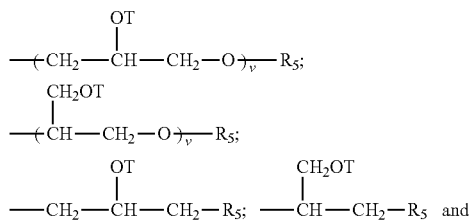

wherein each v in said organosilicone is an integer from 1 to about 10, in one aspect, v is an integer from 1 to about 5 and the sum of all v indices in each Q in the said organosilicone is an integer from 1 to about 30 or from 1 to about 20 or even from 1 to about 10.

In another embodiment, the silicone may be chosen from a random or blocky organosilicone polymer having the following formula:

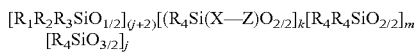

wherein
j is an integer from 0 to about 98; in one aspect j is an integer from 0 to about 48; in one aspect, j is 0;
k is an integer from 0 to about 200; when k=0, at least one of R$_1$, R$_2$ or R$_3$═X—Z, in one aspect, k is an integer from 0 to about 50
m is an integer from 4 to about 5,000; in one aspect m is an integer from about 10 to about 4,000; in another aspect m is an integer from about 50 to about 2,000;

R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy and X—Z;
each R$_4$ is independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy and C$_1$-C$_{32}$ substituted alkoxy;
each X comprises of a substituted or unsubstituted divalent alkylene radical comprising 2-12 carbon atoms; in one aspect each X is independently selected from the group consisting of —(CH$_2$)$_s$—O—; —CH$_2$—CH(OH)—CH$_2$—O—;

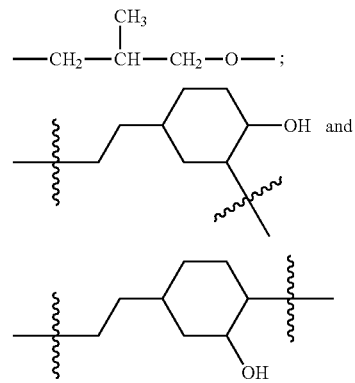

wherein each s independently is an integer from about 2 to about 8, in one aspect s is an integer from about 2 to about 4;
At least one Z in the said organosiloxane is selected from the group consisting of R$_5$;

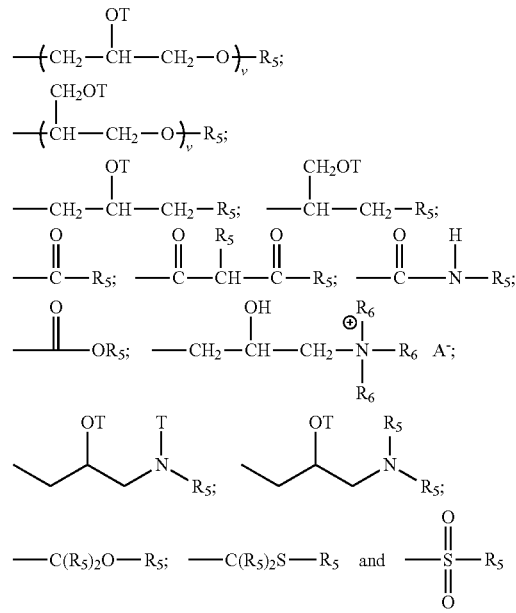

provided that when X is

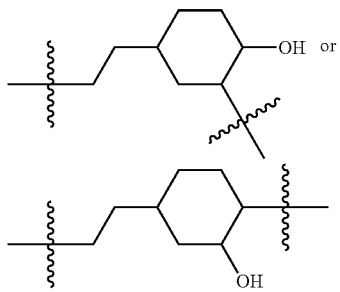

then Z=—OR$_5$ or

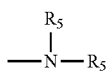

wherein A$^-$ is a suitable charge balancing anion. In one aspect A$^-$ is selected from the group consisting of Cl$^-$, Br$^-$, I$^-$, methylsulfate, toluene sulfonate, carboxylate and phosphate and each additional Z in said organosilicone is independently selected from the group comprising of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, R$_5$,

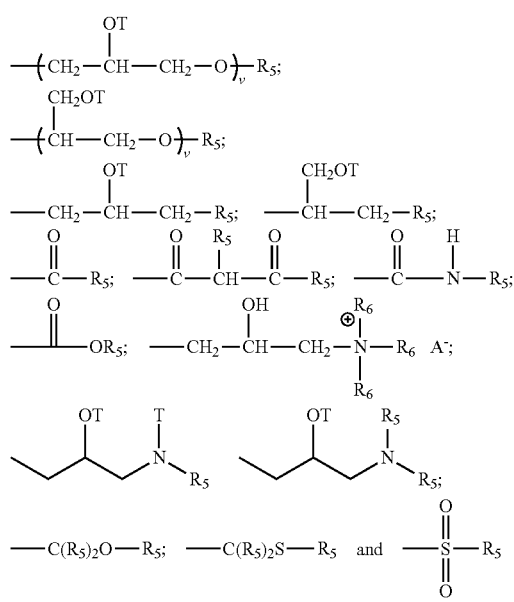

provided that when X is

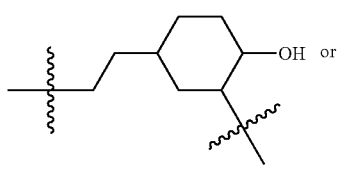

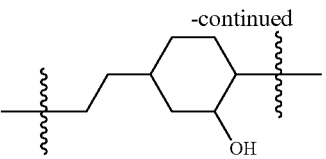

then Z=—OR$_5$ or

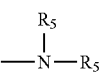

each R$_5$ is independently selected from the group consisting of H; C$_1$-C$_{32}$ alkyl; C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl or C$_6$-C$_{32}$ alkylaryl, or C$_6$-C$_{32}$ substituted alkylaryl, —(CHR$_6$—CHR$_6$—O—)$_w$—CHR$_6$—CHR$_6$-L and siloxyl residue wherein each L is independently selected from —O—C(O)—R$_7$ or —O—R$_7$;

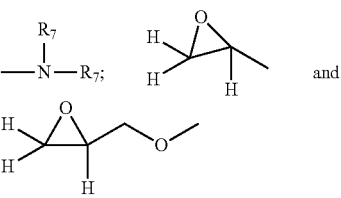

w is an integer from 0 to about 500, in one aspect w is an integer from 0 to about 200, one aspect w is an integer from 0 to about 50;

each R$_6$ is independently selected from H or C$_1$-C$_{18}$ alkyl;

each R$_7$ is independently selected from the group consisting of H; C$_1$-C$_{32}$ alkyl; C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted aryl, and a siloxyl residue;

each T is independently selected from H;

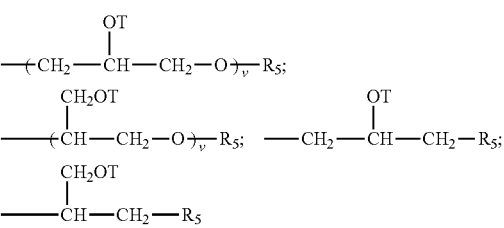

wherein each v in said organosilicone is an integer from 1 to about 10, in one aspect, v is an integer from 1 to about 5 and the sum of all v indices in each Z in the said organosilicone is an integer from 1 to about 30 or from 1 to about 20 or even from 1 to about 10.

In one embodiment, the silicone is one comprising a relatively high molecular weight. A suitable way to describe the molecular weight of a silicone includes describing its viscosity. A high molecular weight silicone is one having a viscosity of from about 10 cSt to about 3,000,000 cSt, or from about 100 cSt to about 1,000,000 cSt, or from about 1,000 cSt to about 600,000 cSt, or even from about 6,000 cSt to about 300,000 cSt.

In one embodiment, the silicone comprises a blocky cationic organopolysiloxane having the formula:

$M_w D_x T_y Q_z$ wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$ or G$_3$, and G$_1$, G$_2$, and G$_3$ are each independently selected from the formula:

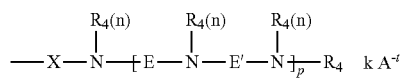

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O; each R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;
E comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;
E' comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O;
p is an integer independently selected from 1 to 50;
n is an integer independently selected from 1 or 2;
when at least one of G$_1$, G$_2$, or G$_3$ is positively charged, A$^{-t}$ is a suitable charge balancing anion or anions such that the total charge, k, of the charge-balancing anion or anions is equal to and opposite from the net charge on the moiety G$_1$, G$_2$ or G$_3$, wherein t is an integer independently selected from 1, 2, or 3; and k≤(p*2/t)+1; such that the total number of cationic charges balances the total number of anionic charges in the organopolysiloxane molecule;
and wherein at least one E does not comprise an ethylene moiety.

Surfactants

In some examples, the additional surfactant comprises one or more anionic surfactants. In some examples, the additional surfactant may consist essentially of, or even consist of one or more anionic surfactants.

Specific, non-limiting examples of suitable anionic surfactants include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates.

Alkoxylated alkyl sulfate materials comprise ethoxylated alkyl sulfate surfactants, also known as alkyl ether sulfates or alkyl polyethoxylate sulfates. Examples of ethoxylated alkyl sulfates include water-soluble salts, particularly the alkali metal, ammonium and alkylolammonium salts, of organic sulfuric compounds having in their molecular structure an alkyl group containing from about 8 to about 30 carbon atoms and a sulfonic acid and its salts. (Included in the term "alkyl" is the alkyl portion of acyl groups. In some examples, the alkyl group contains from about 15 carbon atoms to about 30 carbon atoms. In other examples, the alkyl ether sulfate surfactant may be a mixture of alkyl ether sulfates, said mixture having an average (arithmetic mean) carbon chain length within the range of about 12 to 30 carbon atoms, and in some examples an average carbon chain length of about 12-15 carbon atoms, and an average (arithmetic mean) degree of ethoxylation of from about 1 mol to 4 mols of ethylene oxide, and in some examples an average (arithmetic mean) degree of ethoxylation of about 1.8 mols to about 4 mols of ethylene oxide. In further examples, the alkyl ether sulfate surfactant may have a carbon chain length between about 10 carbon atoms to about 18 carbon atoms, and a degree of ethoxylation of from about 1 to about 6 mols of ethylene oxide. In yet further examples, the alkyl ether sulfate surfactant may contain a peaked ethoxylate distribution, Non-ethoxylated alkyl sulfates may also be added to the disclosed cleaning compositions and used as an anionic surfactant component. Examples of non-alkoxylated, e.g., non-ethoxylated, alkyl sulfate surfactants include those produced by the sulfation of higher C$_8$-C$_{20}$ fatty alcohols. In some examples, primary alkyl sulfate surfactants have the general formula: ROSO$_3^-$ M$^+$, wherein R is typically a linear C$_8$-C$_{20}$ hydrocarbyl group, which may be straight chain or branched chain, and M is a water-solubilizing cation. In some examples, R is a C$_{10}$-C$_{15}$ alkyl, and M is an alkali metal. In other examples, R is a C$_{12}$-C$_{14}$ alkyl and M is sodium.

Other useful anionic surfactants can include the alkali metal salts of alkyl benzene sulfonates, in which the alkyl group contains from about 9 to about 15 carbon atoms, in straight chain (linear) or branched chain configuration. In some examples, the alkyl group is linear. Such linear alkylbenzene sulfonates are known as "LAS." In other examples, the linear alkylbenzene sulfonate may have an average number of carbon atoms in the alkyl group of from about 11 to 14. In a specific example, the linear straight chain alkyl benzene sulfonates may have an average number of carbon atoms in the alkyl group of about 11.8 carbon atoms, which may be abbreviated as C11.8 LAS.

Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

The detersive surfactant may be a mid-chain branched detersive surfactant, in one aspect, a mid-chain branched anionic detersive surfactant, in one aspect, a mid-chain branched alkyl sulphate and/or a mid-chain branched alkyl benzene sulphonate, for example, a mid-chain branched alkyl sulphate. In one aspect, the mid-chain branches are $C_{1-4}$ alkyl groups, typically methyl and/or ethyl groups.

Other anionic surfactants useful herein are the water-soluble salts of: paraffin sulfonates and secondary alkane sulfonates containing from about 8 to about 24 (and in some examples about 12 to 18) carbon atoms; alkyl glyceryl ether sulfonates, especially those ethers of $C_{8-18}$ alcohols (e.g., those derived from tallow and coconut oil). Mixtures of the alkylbenzene sulfonates with the above-described paraffin sulfonates, secondary alkane sulfonates and alkyl glyceryl ether sulfonates are also useful. Further suitable anionic surfactants include methyl ester sulfonates and alkyl ether carboxylates.

The anionic surfactants may exist in an acid form, and the acid form may be neutralized to form a surfactant salt. Typical agents for neutralization include metal counterion bases, such as hydroxides, e.g., NaOH or KOH. Further suitable agents for neutralizing anionic surfactants in their acid forms include ammonia, amines, or alkanolamines. Non-limiting examples of alkanolamines include monoethanolamine, diethanolamine, triethanolamine, and other linear or branched alkanolamines known in the art; suitable alkanolamines include 2-amino-1-propanol, 1-aminopropanol, monoisopropanolamine, or 1-amino-3-propanol. Amine neutralization may be done to a full or partial extent, e.g., part of the anionic surfactant mix may be neutralized with sodium or potassium and part of the anionic surfactant mix may be neutralized with amines or alkanolamines.

Nonionic Surfactants

In some aspects, the additional surfactant comprises one or more nonionic surfactants. In certain aspects, the detergent composition comprises from about 0.1% to about 40%, by weight of the composition, of an additional surfactant selected from one or more nonionic surfactants. In certain aspects, the detergent composition comprises from about 0.1% to about 15%, by weight of the composition, of an additional surfactant selected from one or more nonionic surfactants. In further aspects, the detergent composition comprises from about 0.3% to about 10%, by weight of the composition, of an additional surfactant selected from one or more nonionic surfactants.

Suitable nonionic surfactants useful herein can comprise any conventional nonionic surfactant. These can include, for e.g., alkoxylated fatty alcohols and amine oxide surfactants. In some examples, the cleaning compositions may contain an ethoxylated nonionic surfactant. The nonionic surfactant may be selected from the ethoxylated alcohols and ethoxylated alkyl phenols of the formula $R(OC_2H_4)_nOH$, wherein R is selected from the group consisting of aliphatic hydrocarbon radicals containing from about 8 to about 17 carbon atoms and alkyl phenyl radicals in which the alkyl groups contain from about 8 to about 12 carbon atoms, and the average value of n is from about 5 to about 15. In one example, the nonionic surfactant is selected from ethoxylated alcohols having an average of about 24 carbon atoms in the alcohol and an average degree of ethoxylation of about 9 moles of ethylene oxide per mole of alcohol.

Other non-limiting examples of nonionic surfactants useful herein include: $C_8$-$C_{18}$ alkyl ethoxylates, such as, NEODOL® nonionic surfactants from Shell; $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, alkylpolysaccharides, polyhydroxy fatty acid amides and ether capped poly(oxyalkylated) alcohol surfactants Suitable nonionic detersive surfactants also include alkyl polyglucoside and alkyl alkoxylated alcohol. Suitable nonionic surfactants also include those sold under the tradename Lutensol® from BASF.

In some aspects, the nonionic surfactant is selected from alkyl alkoxylated alcohols, such as a $C_{8-18}$ alkyl alkoxylated alcohol, for example, a $C_{8-18}$ alkyl ethoxylated alcohol. The alkyl alkoxylated alcohol may have an average degree of alkoxylation of from about 1 to about 50, or from about 1 to about 30, or from about 1 to about 20, or from about 1 to about 10. In certain aspects, the alkyl alkoxylated alcohol is a $C_{8-18}$ alkyl ethoxylated alcohol having an average degree of ethoxylation of from about 1 to about 10, or from about 1 to about 7, or from about 1 to about 5, or from about 3 to about 7. The alkyl alkoxylated alcohol can be linear or branched, substituted or unsubstituted.

Cationic Surfactants

In some examples, the additional surfactant comprises one or more cationic surfactants.

In certain aspects, the detergent composition comprises from about 0.1% to about 10%, by weight of the composition, of an additional surfactant selected from one or more cationic surfactants. In certain aspects, the detergent composition comprises from about 0.1% to about 7%, by weight of the composition, of an additional surfactant selected from one or more cationic surfactants. In further aspects, the detergent composition comprises from about 0.3% to about 5%, by weight of the composition, of an additional surfactant selected from one or more cationic surfactants. In some aspects, the cleaning compositions of the invention are substantially free of cationic surfactants and surfactants that become cationic below a pH of 7 or below a pH of 6.

Non-limiting examples of cationic surfactants include: the quaternary ammonium surfactants, which can have up to 26 carbon atoms include: alkoxylate quaternary ammonium (AQA) surfactants, dimethyl hydroxyethyl lauryl ammonium chloride; polyamine cationic surfactants; cationic ester surfactants and amino surfactants, specifically amido propyldimethyl amine (APA) and/or trimethylammonium $C_{8-16}$ alkyl salt.

Suitable cationic detersive surfactants also include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

$(R)(R_1)(R_2)(R_3)N^+X^-$ wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Zwitterionic Surfactants

Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. Specific examples include $C_8$ to $C_{18}$ (for example from $C_{12}$ to $C_{18}$) amine oxides and sulfo and hydroxy betaines, such as N-alkyl-N,N-dimethylamino-1-propane sulfonate where the alkyl group can be $C_8$ to $C_{18}$ and in certain embodiments from $C_{10}$ to $C_{14}$.

Amphoteric Surfactants

Examples of amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, typically from about 8 to about 18 carbon atoms, and at least one of the aliphatic substituents contains an anionic water-solubilizing group, e.g. carboxy, sulfonate, sulfate. Examples of compounds falling within this definition are sodium 3-(dodecylamino)propionate, sodium 3-(dodecylamino) propane-1-sulfonate, sodium 2-(dodecylamino)ethyl sulfate, sodium 2-(dimethylamino) octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis (2-hydroxyethyl)-2-sulfato-3-dodecoxypropylamine. Suitable amphoteric surfactants also include sarcosinates, glycinates, taurinates, and mixtures thereof.

Branched Surfactants

In some examples, the surfactant may be a branched surfactant, Suitable branched surfactants include anionic branched surfactants selected from branched sulphate or branched sulphonate surfactants, e.g., branched alkyl sulphate, branched alkyl alkoxylated sulphate, and branched alkyl benzene sulphonates, comprising one or more random alkyl branches, e.g., $C_{1-4}$ alkyl groups, typically methyl and/or ethyl groups.

In some aspects, the branched detersive surfactant is a mid-chain branched detersive surfactant, typically, a mid-chain branched anionic detersive surfactant, for example, a mid-chain branched alkyl sulphate and/or a mid-chain branched alkyl benzene sulphonate. In some aspects, the detersive surfactant is a mid-chain branched alkyl sulphate. In some aspects, the mid-chain branches are $C_{1-4}$ alkyl groups, typically methyl and/or ethyl groups.

Enzymes

The cleaning compositions described herein may comprise one or more enzymes which provide cleaning performance and/or fabric care benefits. Examples of suitable enzymes include, but are not limited to, hemicellulases, peroxidases, proteases, cellulases, xylanases, lipases, xyloglucanase, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a detergent composition, the aforementioned additional enzymes may be present at levels from about 0.00001% to about 2%, from about 0.0001% to about 1% or even from about 0.001% to about 0.5% enzyme protein by weight of the detergent composition.

In one aspect preferred enzymes would include a protease. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii.*

(b) trypsin-type or chymotrypsin-type proteases, such as trypsin (e.g., of porcine or bovine origin), including the *Fusarium* protease.

(c) metalloproteases, including those derived from *Bacillus amyloliquefaciens* Preferred proteases include those derived from *Bacillus gibsonii* or *Bacillus Lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus* subtilisin with mutations A230V+S256G+S259N) from Kao.

Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis,* or other *Bacillus* sp., such as *Bacillus* sp. NCIB 12289, NCIB 12512, NCIB 12513, DSM 9375, DSM 12368, DSMZ no. 12649, KSM AP1378, KSM K36 or KSM K38. Preferred amylases include:

(a) the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants with one or more substitutions in the following positions versus the AA560 enzyme listed as SEQ ID No. 12:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp.707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(e) variants described in WO 09/149130, preferably those exhibiting at least 90% identity with SEQ ID NO: 1 or SEQ ID NO:2 in WO 09/149130, the wild-type enzyme from *Geobacillus* Stearophermophilus or a truncated version thereof.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

In one aspect, such enzymes may be selected from the group consisting of: lipases, including "first cycle lipases". In one aspect, the lipase is a first-wash lipase, preferably a variant of the wild-type lipase from *Thermomyces lanuginosus* comprising one or more of the T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex® and Lipolex®.

In one aspect, other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403 B2 and mixtures thereof. Suitable endoglucanases are sold under the tradenames Celluclean® and Whitezyme® (Novozymes A/S, Bagsvaerd, Denmark).

Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Enzyme Stabilizing System

The enzyme-containing compositions described herein may optionally comprise from about 0.001% to about 10%, in some examples from about 0.005% to about 8%, and in other examples, from about 0.01% to about 6%, by weight of the composition, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, chlorine bleach scavengers and mixtures thereof, and are designed to address different stabilization problems depending on the type and physical form of the cleaning composition. In the case of aqueous detergent compositions comprising protease, a reversible protease inhibitor, such as a boron compound, including borate, 4-formyl phenylboronic acid, phenylboronic acid and derivatives thereof, or compounds such as calcium formate, sodium formate and 1,2-propane diol may be added to further improve stability.

Builders

The cleaning compositions of the present invention may optionally comprise a builder. Built cleaning compositions typically comprise at least about 1% builder, based on the total weight of the composition. Liquid cleaning compositions may comprise up to about 10% builder, and in some examples up to about 8% builder, of the total weight of the composition. Granular cleaning compositions may comprise up to about 30% builder, and in some examples up to about 5% builder, by weight of the composition.

Builders selected from aluminosilicates (e.g., zeolite builders, such as zeolite A, zeolite P, and zeolite MAP) and silicates assist in controlling mineral hardness in wash water, especially calcium and/or magnesium, or to assist in the removal of particulate soils from surfaces. Suitable builders may be selected from the group consisting of phosphates, such as polyphosphates (e.g., sodium tri-polyphosphate), especially sodium salts thereof; carbonates, bicarbonates, sesquicarbonates, and carbonate minerals other than sodium carbonate or sesquicarbonate; organic mono-, di-, tri-, and tetracarboxylates, especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing cleaning compositions. Additional suitable builders may be selected from citric acid, lactic acid, fatty acid, polycarboxylate builders, for example, copolymers of acrylic acid, copolymers of acrylic acid and maleic acid, and copolymers of acrylic acid and/or maleic acid, and other suitable ethylenic monomers with various types of additional functionalities. Also suitable for use as builders herein are synthesized crystalline ion exchange materials or hydrates thereof having chain structure and a composition represented by the following general anhydride form: $x(M_2O).ySiO_2.zM'O$ wherein M is Na and/or K, M' is Ca and/or Mg; y/x is 0.5 to 2.0; and z/x is 0.005 to 1.0

Alternatively, the composition may be substantially free of builder.

Structurant/Thickeners i. Di-benzylidene Polyol Acetal Derivative

The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. In one aspect, the DBPA derivative may comprise a dibenzylidene sorbitol acetal derivative (DBS). Said DBS derivative may be selected from the group consisting of: 1,3:2,4-dibenzylidene sorbitol; 1,3:2,4-di(p-methylbenzylidene) sorbitol; 1,3:2,4-di(p-chlorobenzylidene) sorbitol; 1,3:2,4-di(2,4-dimethyldibenzylidene) sorbitol; 1,3:2,4-di(p-ethylbenzylidene) sorbitol; and 1,3:2,4-di(3,4-dimethyldibenzylidene) sorbitol or mixtures thereof.

ii. Bacterial Cellulose

The fluid detergent composition may also comprise from about 0.005% to about 1% by weight of a bacterial cellulose network. The term "bacterial cellulose" encompasses any type of cellulose produced via fermentation of a bacteria of the genus *Acetobacter* such as CELLULON® by CPKelco U.S. and includes materials referred to popularly as microfibrillated cellulose, reticulated bacterial cellulose, and the like. In one aspect, said fibres have cross sectional dimensions of 1.6 nm to 3.2 nm by 5.8 nm to 133 nm. Additionally, the bacterial cellulose fibres have an average microfibre length of at least about 100 nm, or from about 100 to about 1,500 nm. In one aspect, the bacterial cellulose microfibres have an aspect ratio, meaning the average microfibre length divided by the widest cross sectional microfibre width, of from about 100:1 to about 400:1, or even from about 200:1 to about 300:1.

iii. Coated Bacterial Cellulose

In one aspect, the bacterial cellulose is at least partially coated with a polymeric thickener. In one aspect the at least partially coated bacterial cellulose comprises from about 0.1% to about 5%, or even from about 0.5% to about 3%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

iv. Cellulose Fibers Non-Bacterial Cellulose Derived

In one aspect, the composition may further comprise from about 0.01 to about 5% by weight of the composition of a cellulosic fiber. Said cellulosic fiber may be extracted from vegetables, fruits or wood. Commercially available examples are Avicel® from FMC, Citri-Fi from Fiberstar or Betafib from Cosun.

v. Non-Polymeric Crystalline Hydroxyl-Functional Materials

In one aspect, the composition may further comprise from about 0.01 to about 1% by weight of the composition of a non-polymeric crystalline, hydroxyl functional structurant. Said non-polymeric crystalline, hydroxyl functional structurants generally may comprise a crystallizable glyceride which can be pre-emulsified to aid dispersion into the final fluid detergent composition. In one aspect, crystallizable glycerides may include hydrogenated castor oil or "HCO" or derivatives thereof, provided that it is capable of crystallizing in the liquid detergent composition.

vi. Polymeric Structuring Agents

Fluid detergent compositions of the present invention may comprise from about 0.01% to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In one aspect, said polycarboxylate polymer is a polyacrylate, polymethacrylate or mixtures thereof. In another aspect, the polyacrylate is a copolymer of unsaturated mono- or di-carbonic acid and $C_1$-$C_{30}$ alkyl ester of the (meth)acrylic acid. Said copolymers are available from Noveon inc under the tradename Carbopol Aqua 30.

vii. Di-Amido-Gellants

In one aspect, the external structuring system may comprise a di-amido gellant having a molecular weight from about 150 g/mol to about 1,500 g/mol, or even from about 500 g/mol to about 900 g/mol. Such di-amido gellants may comprise at least two nitrogen atoms, wherein at least two of said nitrogen atoms form amido functional substitution groups. In one aspect, the amido groups are different. In another aspect, the amido functional groups are the same. Non-limiting examples of useful di-amido gellants are:

N,N'-(2S,2'S)— 1,1'(dodecane-1,12-diylbis(azanediyl))bis (3-methyl-1-oxobutane-2,1-diyl)diisonicotinamide;

dibenzyl (2S,2'S)-1,1'-(propane-1,3-diylbis(azanediyl))bis (3-methyl-1-oxobutane-2,1-diyl)dicarbamate; and dibenzyl (2S,2'S)-1,1'-(dodecane-1,12-diylbis(azanediyl)) bis(1-oxo-3-phenylpropane-2,1-diyl)dicarbamate.

Polymeric Dispersing Agents

The detergent composition may comprise one or more polymeric dispersing agents. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent composition may comprise one or more amphiphilic cleaning polymers such as the compound having the following general structure: bis(($C_2H_5O$)($C_2H_4O$)n) ($CH_3$)—$N^+$—$C_xH_{2x}$—$N^+$—($CH_3$)-bis(($C_2H_5O$)($C_2H_4O$)n), wherein n=from 20 to 30, and x=from 3 to 8, or sulphated or sulphonated variants thereof.

The detergent composition may comprise amphiphilic alkoxylated grease cleaning polymers which have balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, for example, having an inner polyethylene oxide block and an outer polypropylene oxide block. Such compounds may include, but are not limited to, ethoxylated polyethyleneimine, ethoxylated hexamethylene diamine, and sulfated versions thereof. Polypropoxylated derivatives may also be included. A wide variety of amines and polyalklyeneimines can be alkoxylated to various degrees. A useful example is 600 g/mol polyethyleneimine core ethoxylated to 20 EO groups per NH and is available from BASF. The cleaning compositions described herein may comprise from about 0.1% to about 10%, and in some examples, from about 0.1% to about 8%, and in other examples, from about 0.1% to about 6%, by weight of the cleaning composition, of alkoxylated polyamines.

Alkoxylated polycarboxylates such as those prepared from polyacrylates are useful herein to provide additional grease removal performance. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. The detergent compositions described herein may comprise from about 0.1% to about 10%, and in some examples, from about 0.25% to about 5%, and in other examples, from about 0.3% to about 2%, by weight of the cleaning composition, of alkoxylated polycarboxylates.

Suitable amphilic graft co-polymer preferable include the amphilic graft co-polymer comprises (i) polyethylene glycol backbone; and (ii) and at least one pendant moiety selected from polyvinyl acetate, polyvinyl alcohol and mixtures thereof. A preferred amphilic graft co-polymer is Sokalan® HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is typically about 6000 and the weight ratio of the polyethylene oxide to polyvinyl acetate is about 40 to 60 and no more than 1 grafting point per 50 ethylene oxide units.

Carboxylate polymer—The detergent compositions of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da.

Soil release polymer—The detergent compositions of the present invention may also include one or more soil release polymers having a structure as defined by one of the following structures (I), (II) or (III):

Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;

$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic polymer—The consumer products of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

Amines

Various amines may be used in the cleaning compositions described herein for added removal of grease and particulates from soiled materials. The detergent compositions described herein may comprise from about 0.1% to about 10%, in some examples, from about 0.1% to about 4%, and in other examples, from about 0.1% to about 2%, by weight of the cleaning composition, of additional amines Non-limiting examples of amines include, but are not limited to, polyamines, oligoamines, triamines, diamines, pentamines, tetraamines, polyetheramines, or combinations thereof. Specific examples of suitable additional amines include tetraethylenepentamine, triethylenetetraamine, diethylenetriamine, polyetheramines, or a mixture thereof. A suitable polyetheramine is represented by the structure of Formula (I):

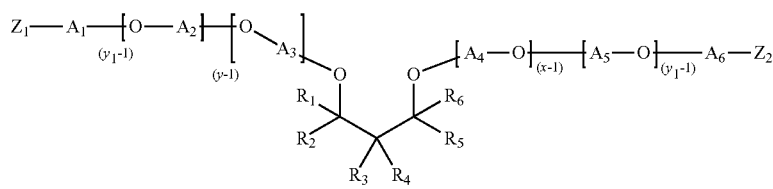

Formula (I)

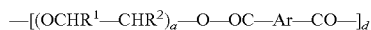
(I)

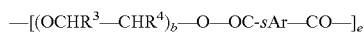
(II)

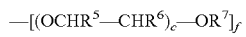
(III)

wherein:

a, b and c are from 1 to 200;

d, e and f are from 1 to 50;

Ar is a 1,4-substituted phenylene;

sAr is 1,3-substituted phenylene substituted in position 5 with $SO_3Me$;

where each of $R_1$-$R_6$ is independently selected from H, alkyl, cycloalkyl, aryl, alkylaryl, or arylalkyl, where at least one of $R_1$-$R_6$ is different from H, typically at least one of $R_1$-$R_6$ is an alkyl group having 2 to 8 carbon atoms, each of $A_1$-$A_6$ is independently selected from linear or branched alkylenes having 2 to 18 carbon atoms, typically 2 to 10 carbon atoms, more typically, 2 to 5 carbon atoms, each of $Z_1$-$Z_2$ is independently selected from OH or $NH_2$, where at least one of $Z_1$-$Z_2$ is $NH_2$, typically each of $Z_1$ and $Z_2$ is $NH_2$, where the sum of x+y is in the range of about 2 to about 200, typically about 2 to about 20 or about 3 to about 20, more typically about 2 to about 10 or about 3 to about 8 or about 4 to about 6, where x≥1 and y≥1, and the sum of $x_1+y_1$ is in the range of about 2 to about 200, typically about 2 to about 20 or about 3 to about 20, more typically about 2 to about 10 or about 3 to about 8 or about 2 to about 4, where $x_1 \geq 1$ and $y_1 \geq 1$. Another suitable polyetheramine is represented by the structure of Formula (II):

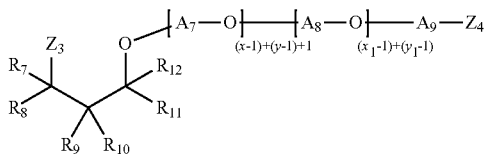

Formula (II)

where each of $R_7$-$R_{12}$ is independently selected from H, alkyl, cycloalkyl, aryl, alkylaryl, or arylalkyl, where at least one of $R_7$-$R_{12}$ is different from H, typically at least one of $R_7$-$R_{12}$ is an alkyl group having 2 to 8 carbon atoms, each of $A_7$-$A_9$ is independently selected from linear or branched alkylenes having 2 to 18 carbon atoms, typically 2 to 10 carbon atoms, more typically, 2 to 5 carbon atoms, each of $Z_3$-$Z_4$ is independently selected from OH or $NH_2$, where at least one of $Z_3$-$Z_4$ is $NH_2$, typically each of $Z_3$ and $Z_4$ is $NH_2$, where the sum of x+y is in the range of about 2 to about 200, typically about 2 to about 20 or about 3 to about 20, more typically about 2 to about 10 or about 3 to about 8 or about 2 to about 4, where $x \geq 1$ and $y \geq 1$, and the sum of $x_1+y_i$ is in the range of about 2 to about 200, typically about 2 to about 20 or about 3 to about 20, more typically about 2 to about 10 or about 3 to about 8 or about 2 to about 4, where $x_1 \geq 1$ and $y_1 \geq 1$.

Another suitable polyetheramine is represented by the structure of Formula III:

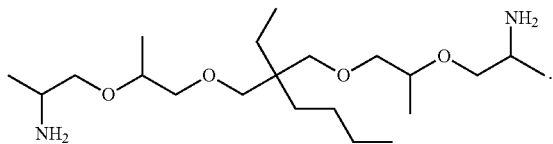

Formula (III)

Solvents—suitable solvents include, but are not limited to, water, alcohol, paraffins, glycols, glycerols, and mixtures thereof.

Bleaching Agents—The detergent compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the detergent compositions of the present invention may comprise from about 0.1% to about 50% or even from about 0.1% to about 25% bleaching agent by weight of the detergent composition. Examples of suitable bleaching agents include:

(1) photobleaches for example sulfonated zinc phthalocyanine sulfonated aluminium phthalocyanines, xanthene dyes and mixtures thereof;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone®, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall fabric and home care product and are typically incorporated into such fabric and home care products as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). While any suitable bleach activator may be employed, in one aspect of the invention the subject detergent composition may comprise NOBS, TAED or mixtures thereof.

When present, the peracid and/or bleach activator is generally present in the detergent composition in an amount of from about 0.1 to about 60 wt %, from about 0.5 to about 40 wt % or even from about 0.6 to about 10 wt % based on the fabric and home care product. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Bleach Catalysts—

The detergent compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

In one aspect, the bleach catalyst has a structure corresponding to general formula below:

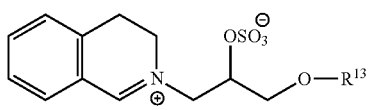

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl;

Brighteners

Optical brighteners or other brightening or whitening agents may be incorporated at levels of from about 0.01% to about 1.2%, by weight of the composition, into the cleaning compositions described herein. Commercial fluorescent brighteners suitable for the present invention can be classified into subgroups, including but not limited to: derivatives of stilbene, pyrazoline, coumarin, benzoxazoles, carboxylic acid, methinecyanines, dibenzothiophene-5,5-dioxide, azoles, 5- and 6-membered-ring heterocycles, and other miscellaneous agents.

In some examples, the fluorescent brightener herein comprises a compound of formula (1):

(1)

wherein: $X_1$, $X_2$, $X_3$, and $X_4$ are —N(R$^1$)R$^2$, wherein R$^1$ and R$^2$ are independently selected from a hydrogen, a phenyl, hydroxyethyl, or an unsubstituted or substituted $C_1$-$C_8$ alkyl, or —N(R$^1$)R$^2$ form a heterocyclic ring, preferably R$^1$ and R$^2$ are independently selected from a hydrogen or phenyl, or —N(R$^1$)R$^2$ form a unsubstituted or substituted morpholine ring; and M is a hydrogen or a cation, preferably M is sodium or potassium, more preferably M is sodium.

In some examples, the fluorescent brightener is selected from the group consisting of disodium 4,4'-bis{[4-anilino-6-morpholino-s-triazin-2-yl]-amino}-2,2'-stilbenedisulfonate (brightener 15, commercially available under the tradename Tinopal AMS-GX by Ciba Geigy Corporation), disodium4,4'-bis{[4-anilino-6-(N-2-bis-hydroxyethyl)-s-triazine-2-yl]-amino}-2,2'-stilbenedisulonate (commercially available under the tradename Tinopal UNPA-GX by Ciba-Geigy Corporation), disodium 4,4'-bis{[4-anilino-6-(N-2-hydroxyethyl-N-methylamino)-s-triazine-2-yl]-amino}-2,2'-stilbenedisulfonate (commercially available under the tradename Tinopal 5BM-GX by Ciba-Geigy Corporation). More preferably, the fluorescent brightener is disodium 4,4'-bis{[4-anilino-6-morpholino-s-triazin-2-yl]-amino}-2,2'-stilbenedisulfonate. The brighteners may be added in particulate form or as a premix with a suitable solvent, for example nonionic surfactant, monoethanolamine, propane diol.

Water-Soluble Film

The compositions of the present invention may also be encapsulated within a water-soluble film. Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000. Mixtures of polymers can also be used as the pouch material. Naturally, different film material and/or films of different thickness may be employed in making the compartments of the present invention. A benefit in selecting different films is that the resulting compartments may exhibit different solubility or release characteristics.

Most preferred film materials are PVA films known under the MonoSol trade reference M8630, M8900, H8779.

The film material herein can also comprise one or more additive ingredients. For example, it can be beneficial to add plasticizers, for example glycerol, ethylene glycol, diethyleneglycol, propylene glycol, sorbitol and mixtures thereof. Other additives include functional detergent additives to be delivered to the wash water, for example organic polymeric dispersants.

Suds Boosters

If high sudsing is desired, suds boosters such as the $C_{10}$-$C_{16}$ alkanolamides may be incorporated into the cleaning compositions at a concentration ranging from about 1% to about 10% by weight of the cleaning composition. Some examples include the $C_{10}$-$C_{14}$ monoethanol and diethanol amides. If desired, water-soluble magnesium and/or calcium salts such as $MgCl_2$, $MgSO_4$, $CaCl_2$, $CaSO_4$, and the like, may be added at levels of about 0.1% to about 2% by weight of the cleaning composition, to provide additional suds and to enhance grease removal performance.

Conditioning Agents

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof.

The high melting point fatty compound is included in the composition at a level of from about 0.1% to about 40%, preferably from about 1% to about 30%, more preferably from about 1.5% to about 16% by weight of the composition, from about 1.5% to about 8% in view of providing improved conditioning benefits such as slippery feel during the application to wet hair, softness and moisturized feel on dry hair.

The compositions of the present invention may contain a cationic polymer. Concentrations of the cationic polymer in the composition typically range from about 0.05% to about 3%, in another embodiment from about 0.075% to about 2.0%, and in yet another embodiment from about 0.1% to about 1.0%. Suitable cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

The composition of the present invention may include a nonionic polymer as a conditioning agent. Polyalkylene glycols having a molecular weight of more than about 1000 are useful herein. Useful are those having the following general formula:

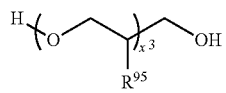

wherein $R^{95}$ is selected from the group consisting of H, methyl, and mixtures thereof. Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

Fabric Hueing Agents

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes and mixtures thereof. In another aspect, suitable small molecule dyes include small molecule dyes selected from the group consisting of C. I. numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used).

Perfumes—

Suitable adjunct perfume raw materials include those perfume raw materials listed in Table 2 below. Such adjunct perfume raw materials may be used in addition to the silicone compounds disclosed in the present specification. For example, such adjunct perfume raw materials may be used to formulate a part or all of a neat perfume.

TABLE 2

Adjunct Perfume Raw Materials:

| Number | Registry Name | Trade Name |
|---|---|---|
| 1 | Propanoic acid, ethyl ester | Ethyl Propionate |
| 2 | Acetic acid, 2-methylpropyl ester | Isobutyl Acetate |
| 3 | Butanoic acid, ethyl ester | Ethyl Butyrate |
| 4 | Butanoic acid, 2-methyl-, ethyl ester | Ethyl-2-Methyl Butyrate |
| 5 | 1-Butanol, 3-methyl-, acetate | Iso Amyl-Acetate |
| 6 | 2-Buten-1-ol, 3-methyl-, acetate | Prenyl Acetate |
| 7 | 3-Hexen-1-ol, acetate, (Z)- | Cis 3 Hexenyl Acetate |
| 8 | Benzoic acid, methyl ester | Methyl Benzoate |
| 9 | Benzeneacetic acid, methyl ester | Methyl Phenyl Acetate |
| 10 | 1,3-Dioxolane-2-acetic acid, 2-methyl-, ethyl ester | Fructone |
| 11 | Acetic acid, (2-methylbutoxy)-, 2-propenyl ester | Allyl Amyl Glycolate |
| 12 | Benzenemethanol, .alpha.-methyl-, acetate | Methyl Phenyl Carbinyl Acetate |
| 13 | Benzeneacetic acid, ethyl ester | Ethyl Phenyl Acetate |
| 14 | Acetic acid, 2-phenylethyl ester | Phenyl Ethyl Acetate |
| 15 | 2-Propenoic acid, 3-phenyl-, methyl ester | Methyl Cinnamate |
| 16 | Acetic acid ethyl ester | Ethyl Acetate |
| 17 | Butanoic acid, 3-oxo-, ethyl ester | Ethyl Acetoacetate |
| 18 | Tricyclo[2.2.1.02,6]heptane, 1-ethyl-3-methoxy- | Neoproxen |
| 19 | Benzene, 1,4-dimethoxy- | Hydroquinone Dimethyl Ether |
| 20 | Carbonic acid, 3-hexenyl methyl ester, (Z)- | Liffarome |
| 21 | Oxirane, 2,2-dimethyl-3-(3-methyl-2,4-pentadienyl)- | Myroxide |

TABLE 2-continued

Adjunct Perfume Raw Materials:

| Number | Registry Name | Trade Name |
|---|---|---|
| 22 | Ethanol, 2-(2-ethoxyethoxy)- | Diethylene Glycol Mono Ethylether |
| 23 | 1,3-Oxathiane, 2-methyl-4-propyl-, cis- | Oxane |
| 24 | Acetic acid, 4-methylphenyl ester | Para Cresyl Acetate |
| 25 | Benzene, (2,2-dimethoxyethyl)- | Phenyl Acetaldehyde Dimethyl Acetal |
| 26 | Propanoic acid, phenylmethyl ester | Benzyl Propionate |
| 27 | 2H-1-Benzopyran-2-one, octahydro- | Octahydro Coumarin |
| 28 | Benzoic acid, 2-hydroxy-, methyl ester | Methyl Salicylate USP |
| 29 | Propanenitrile, 3-(3-hexenyloxy)-, (Z)- | Parmanyl |
| 30 | Benzene, [2-(2-propenyloxy)ethyl]- | LRA 220 |
| 31 | Bicyclo[2.2.1]heptane, 2,2-dimethyl-3-methylene- | Camphene |
| 32 | Bicyclo[3.1.1]heptane, 6,6-dimethyl-2-methylene-, (1S)- | Beta Pinene |
| 33 | Bicyclo[3.1.1]hept-2-ene, 2,6,6-trimethyl- | Alpha Pinene |
| 34 | Propanoic acid, pentyl ester | Amyl Propionate |
| 35 | 1,6-Octadiene, 7-methyl-3-methylene- | Myrcene |
| 36 | Cyclohexene, 1-methyl-4-(1-methylethenyl)- | Dipentene |
| 37 | Cyclohexene, 1-methyl-4-(1-methylethenyl)- | Terpineolene |
| 38 | Acetic acid, hexyl ester | Hexyl Acetate |
| 39 | Benzene, 1-methoxy-4-methyl- | Para Cresyl Methyl Ether |
| 40 | 1-Octen-3-ol, acetate | Amyl Vinyl Carbinyl Acetate |
| 41 | 2-Oxabicyclo[2.2.2]octane, 1,3,3-trimethyl- | Eucalyptol |
| 42 | Butanoic acid, pentyl ester | Amyl Butyrate |
| 43 | Heptanoic acid, ethyl ester | Ethyl Oenanthate |
| 44 | Hexanoic acid, 2-propenyl ester | Allyl Caproate |
| 45 | 3-Hexene, 1-(1-ethoxyethoxy)-, (Z)- | Leaf Acetal |
| 46 | 2-Octynoic acid, methyl ester | Methyl Heptine Carbonate |
| 47 | Benzoic acid, ethyl ester | Ethyl Benzoate |
| 48 | 1-Hexanol, 3,5,5-trimethyl-, acetate | Iso Nonyl Acetate |
| 49 | Heptanoic acid, 2-propenyl ester | Allyl Heptoate |
| 50 | Butanoic acid, 3-hexenyl ester, (Z)- | Cis 3 Hexenyl Butyrate |
| 51 | 1,6-Octadien-3-ol, 3,7-dimethyl-, formate | Linalyl Formate |
| 52 | 3-Octanol, 3,7-dimethyl-, acetate | Tetrahydro Linalyl Acetate |
| 53 | 7-Octen-2-ol, 2,6-dimethyl-, acetate | Dihydro Terpinyl Acetate |
| 54 | 7-Octen-2-ol, 2-methyl-6-methylene-, acetate | Myrcenyl Acetate |
| 55 | 2-Butenoic acid, 2-methyl-, 3-hexenyl ester, (E,Z)- | Cis-3-Hexenyl Tiglate |
| 56 | 1,6-Octadien-3-ol, 3,7-dimethyl-, acetate | Linalyl Acetate |
| 57 | Benzene, 1-methoxy-4-(1-propenyl)-, (E)- | Anethol Usp |
| 58 | 6-Octen-1-ol, 3,7-dimethyl-, formate | Citronellyl Formate |
| 59 | 3-Cyclohexene-1-methanol, .alpha.,.alpha.,4-trimethyl-, acetate | Terpinyl Acetate |
| 60 | 2,6-Octadien-1-ol, 3,7-dimethyl-, formate, (E)- | Geranyl Formate |
| 61 | Bicyclo[2.2.1]heptan-2-ol, 1,3,3-trimethyl-, acetate | Fenchyl Acetate |
| 62 | Bicyclo[2.2.1]heptan-2-ol, 1,7,7-trimethyl-, acetate, exo- | Iso Bornyl Acetate |
| 63 | 2H-Pyran-2-one, tetrahydro-6-pentyl- | Delta Decalactone |
| 64 | 6-Octen-1-ol, 3,7-dimethyl-, acetate | Citronellyl Acetate |
| 65 | 2(3H)-Furanone, 5-hexyldihydro- | Gamma Decalactone |
| 66 | 2,6-Octadien-1-ol, 3,7-dimethyl-, acetate, (E)- | Geranyl Acetate |
| 67 | 2H-Pyran-2-one, tetrahydro-6-(3-pentenyl)- | Jasmolactone |
| 68 | Cyclohexanol, 5-methyl-2-(1-methylethyl)-, acetate,(1.alpha.,2.beta.,5.alpha.)- | Menthyl Acetate |
| 69 | 2,6-Octadien-1-ol, 3,7-dimethyl-, acetate, (Z)- | Neryl Acetate |
| 70 | Benzeneethanol, .alpha.,.alpha.-dimethyl-, acetate | Dimethyl Benzyl Carbinyl Acetate |
| 71 | Propanoic acid, 2-methyl-, 1,3-dimethyl-3-butenyl ester | Iso Pentyrate |
| 72 | Propanoic acid, 2-methyl-, 3-hexenyl ester, (Z)- | Verdural B Extra |
| 73 | 2H-Pyran, tetrahydro-4-methyl-2-(2-methyl-1-propenyl)- | Methyl Iso Butenyl Tetrahydro Pyran |
| 74 | Hexanoic acid, 2-methylpropyl ester | Iso Butyl Caproate |
| 75 | Cyclohexane, 3-ethoxy-1,1,5-trimethyl- | Herbavert |
| 76 | Propanoic acid, 2,2-dimethyl-, hexyl ester | Hexyl Neo Pentanoate |
| 77 | Butanoic acid, 2-methyl-, hexyl ester | Hexyl-2-Methyl Butyrate |
| 78 | Cyclohexaneethanol, acetate | Cyclohexyl Ethyl Acetate |
| 79 | Propanoic acid, 2-methyl-, phenylmethyl ester | Benzyl Iso Butyrate |
| 80 | Propanoic acid, 2-methyl-, 4-methylphenyl ester | Para Cresyl Iso Butyrate |
| 81 | Carbonic acid, 4-cycloocten-1-yl methyl ester | Violiff |
| 82 | 1,6-Octadien-3-ol, 3,7-dimethyl-, propanoate | Linalyl Propionate |
| 83 | Butanoic acid, phenylmethyl ester | Benzyl Butyrate |
| 84 | 4,7-Methano-1H-inden-5-ol, octahydro-, acetate | Dihydro Cyclacet |

TABLE 2-continued

Adjunct Perfume Raw Materials:

| Number | Registry Name | Trade Name |
|---|---|---|
| 85 | Bicyclo[2.2.1]heptan-2-ol, 1,7,7-trimethyl-, propanoate, exo- | Iso Bornyl Propionate |
| 86 | 2,6-Octadienenitrile, 3,7-dimethyl- | Geranyl Nitrile |
| 87 | Benzene, ethenyl- | Styrene |
| 88 | Benzene, methyl(1-methylethyl)- | Cymene Coeur |
| 89 | 1,3,5-Undecatriene | Galbanolene Super |
| 90 | 2-Cyclohexene-1-carboxylic acid, 2,6,6-trimethyl-, methyl ester | Methyl Cyclogeranate |
| 91 | Benzene, (2-bromoethenyl)- | Brom Styrol |
| 92 | Benzene, 1-methoxy-4-(2-propenyl)- | Methyl Chavicol |
| 93 | 1,3-Dioxane, 2-butyl-4,4,6-trimethyl- | Herboxane |
| 94 | 2-Nonynoic acid, methyl ester | Methyl Octine Carbonate |
| 95 | 6-Octenenitrile, 3,7-dimethyl- | Baranyl Nitrile |
| 96 | 1-Hexanol, 5-methyl-2-(1-methylethyl)-, acetate | Tetrahydro Lavandulyl Acetate |
| 97 | Cyclohexanemethanol, .alpha.,3,3-trimethyl-, acetate | Rosamusk |
| 98 | 2,6-Octadiene, 1,1-dimethoxy-3,7-dimethyl- | Citral Dimethyl Acetal |
| 99 | Cyclohexanol, 4-(1,1-dimethylethyl)-, acetate | Tertiary Butyl Cyclohexyl Acetate |
| 100 | Cyclohexanol, 5-methyl-2-(1-methylethenyl)-, acetate, [1R-(1.alpha.,2.beta.,5.alpha.)]- | Iso Pulegol Acetate |
| 101 | Benzene, [(3-methylbutoxy)methyl]- | Iso Amyl Benzyl Ether |
| 102 | 2(3H)-Furanone, 5-hexyldihydro-5-methyl- | Lactojasmon |
| 103 | Benzoic acid, butyl ester | Butyl Benzoate |
| 104 | Bicyclo[3.2.1]octan-8-one, 1,5-dimethyl-, oxime | Buccoxime |
| 105 | Cyclohexanemethanol, .alpha.,3,3-trimethyl-, formate | Aphermate |
| 106 | Dodecanenitrile | Clonal |
| 107 | Cyclohexanepropanoic acid, 2-propenyl ester | Allyl Cyclohexane Propionate |
| 108 | 1,4-Cyclohexanedicarboxylic acid, diethyl ester | Fructalate |
| 109 | 2(3H)-Furanone, 5-heptyldihydro- | Undecalactone |
| 110 | Naphthalene, 2-methoxy- | Beta Naphthol Methyl Ether |
| 111 | 2-Propen-1-ol, 3-phenyl-, acetate | Cinnamyl Acetate |
| 112 | Butanoic acid, 1,1-dimethyl-2-phenylethyl ester | Dimethyl Benzyl Carbinyl Butyrate |
| 113 | 2H-Pyran-2-one, 6-heptyltetrahydro- | Dodecalactone |
| 114 | Oxiranecarboxylic acid, 3-methyl-3-phenyl-, ethyl ester | Ethyl Methyl Phenyl Glycidate |
| 115 | Oxiranecarboxylic acid, 3-phenyl-, ethyl ester | Ethyl Phenyl Glycidate |
| 116 | 4,7-Methano-1H-inden-6-ol, 3a,4,5,6,7,7a-hexahydro-, propanoate | Frutene |
| 117 | 2H-Pyran-4-ol, tetrahydro-3-pentyl-, acetate | Jasmal |
| 118 | Bicyclo[3.1.1]hept-2-ene-2-ethanol, 6,6-dimethyl-, acetate | Nopyl Acetate |
| 119 | Benzenepropanol, .alpha.,.alpha.-dimethyl-, acetate | Phenyl Ethyl Dimethyl Carbinyl Acetate |
| 120 | Propanoic acid, 2-methyl-, 3a,4,5,6,7,7a-hexahydro-4,7-methano-1H- | Cyclabute |
| 121 | Benzenemethanol, ar-methoxy-, acetate | Anisyl Acetate |
| 122 | Bicyclo[2.2.1]hept-5-ene-2-carboxylic acid, 3-(1-methylethyl)-,ethyl ester, (2-endo,3-exo)- | Herbanate Ci |
| 123 | Butanoic acid, 3-methyl-, 2-phenylethyl ester | Beta Phenyl Ethyl Isovalerate |
| 124 | Bicyclo[7.2.0]undec-4-ene, 4,11,11-trimethyl-8-methylene-,[1R-(1R*,4E,9S*)]- | Caryophyllene Extra |
| 125 | 6-Octen-1-ol, 3,7-dimethyl-, propanoate | Citronellyl Propionate |
| 126 | Propanoic acid, decyl ester | N-Decyl Propionate |
| 127 | Cyclohexanol, 1-ethenyl-2-(1-methylpropyl)-, acetate | Dihydro Ambrate |
| 128 | 2-Propenoic acid, 3-phenyl-, ethyl ester | Ethyl Cinnamate |
| 129 | Butanoic acid, 3,7-dimethyl-2,6-octadienyl ester, (E)- | Geranyl Butyrate |
| 130 | Cyclohexadieneethanol, 4-(1-methylethyl)-, formate | Iso Bergamate |
| 131 | Propanoic acid, 2-methyl-, 1-ethenyl-1,5-dimethyl-4-hexenyl ester | Linalyl Iso Butyrate |
| 132 | Propanoic acid, 2-methyl-, 2-phenylethyl ester | Phenyl Ethyl Iso Butyrate |
| 133 | 2-Propenenitrile, 3-phenyl- | Cinnamalva |
| 134 | Benzene, [2-(1-propoxyethoxy)ethyl]- | Acetal R |
| 135 | 1H-2-Benzopyran, 3,4,4a,5,8,8a(or 3,4,4a,7,8,8a)-hexahydro-3,3,6,7- | Bigarade Oxide |
| 136 | Cyclohexene, 4-(1,5-dimethyl-4-hexenylidene)-1-methyl- | Bisabolene |
| 137 | 1H-3a,7-Methanoazulene, octahydro-6-methoxy-3,6,8,8-tetramethyl-,[3R-(3.alpha.,3a.beta.,6.alpha.,7.beta.,8a.alpha.)]- | Cedramber |

TABLE 2-continued

Adjunct Perfume Raw Materials:

| Number | Registry Name | Trade Name |
|---|---|---|
| 138 | 2,6-Octadiene, 1,1-diethoxy-3,7-dimethyl- | Citrathal |
| 139 | Acetaldehyde, [(3,7-dimethyl-6-octenyl)oxy]- | Citronellyl Oxyacetaldehyde |
| 140 | Benzenepropanenitrile, .alpha.-ethenyl-.alpha.-methyl- | Citrowanil B |
| 141 | Cyclohexanol, 2-(1,1-dimethylpropyl)-, acetate | Coniferan |
| 142 | 1,3-Nonanediol, monoacetate | Diasmol |
| 143 | Benzene, 1,1'-methylenebis- | Diphenyl Methane |
| 144 | Benzene, 1,1'-oxybis- | Diphenyl Oxide |
| 145 | 1,6-Octadiene, 3-(1-ethoxyethoxy)-3,7-dimethyl- | Elinthal |
| 146 | 5,8-Methano-2H-1-benzopyran-2-one, 6-ethylideneoctahydro- | Florex |
| 147 | Octanoic acid, 2-acetyl-, ethyl ester | Gelsone |
| 148 | Indeno[1,2-d]-1,3-dioxin, 4,4a,5,9b-tetrahydro- | Indoflor Crist. |
| 149 | Benzeneacetic acid, 2-methylpropyl ester | Iso Butyl Phenylacetate |
| 150 | 2,6-Nonadienenitrile, 3,7-dimethyl- | Lemonile |
| 151 | Undecane, 1,1-dimethoxy-2-methyl- | Methyl Nonyl Acetaldehyde Dimethyl Aceta |
| 152 | Quinoline, 6-methyl- | Para Methyl Quinoline |
| 153 | Propanoic acid, 2-methyl-, 2-phenoxyethyl ester | Phenoxy Ethyl Iso Butyrate |
| 154 | Ethanol, 2-phenoxy-, propanoate | Phenoxy Ethyl Propionate |
| 155 | Benzenemethanol, .alpha.-(trichloromethyl)-, acetate | Trichloromethyl Phenyl Carbinyl Acetate |
| 156 | Phenol, 2-methoxy-4-(methoxymethyl)- | Vaniwhite |
| 157 | Benzene, [2-(3-methylbutoxy)ethyl]- | Phenyl Ether Isamyl Ether (Aka Anther) |
| 158 | 2-Cyclohexene-1-carboxylic acid, 2,3,6,6-tetramethyl-, ethyl ester | Givescone |

Additional Perfume Delivery Technologies—

The consumer products may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

In one aspect, the fluid fabric enhancer composition may comprise from about 0.001% to about 20%, or from about 0.01% to about 10%, or from about 0.05% to about 5%, or even from about 0.1% to about 0.5% by weight of the perfume delivery technology. In one aspect, said perfume delivery technologies may be selected from the group consisting of: perfume microcapsules, pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, and mixtures thereof.

In one aspect, said perfume delivery technology may comprise microcapsules formed by at least partially surrounding a benefit agent with a wall material. Said benefit agent may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, δ-damascone, β-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol; silicone oils, waxes such as polyethylene waxes; essential oils such as fish oils, jasmine, camphor, lavender; skin coolants such as menthol, methyl lactate; vitamins such as Vitamin A and E; sunscreens; glycerine; catalysts such as manganese catalysts or bleach catalysts; bleach particles such as perborates; silicon dioxide particles; antiperspirant actives; cationic polymers and mixtures thereof. Suitable benefit agents can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, polyacrylate esters based materials, gelatin, styrene malic anhydride, polyamides, aromatic alcohols, polyvinyl alcohol and mixtures thereof. In one aspect, said melamine wall material may comprise melamine cross-linked with formaldehyde, melamine-dimethoxyethanol crosslinked with formaldehyde, and mixtures thereof. In one aspect, said polystyrene wall material may comprise polystyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based wall materials may comprise polyacrylate formed from methyl-methacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

In one aspect, said polyacrylate ester based wall materials may comprise polyacrylate esters formed by alkyl and/or glycidyl esters of acrylic acid and/or methacrylic acid, acrylic acid esters and/or methacrylic acid esters which carry hydroxyl and/or carboxy groups, and allylgluconamide, and mixtures thereof.

In one aspect, said aromatic alcohol based wall material may comprise aryloxyalkanols, arylalkanols and oligoalkanolarylethers. It may also comprise aromatic compounds with at least one free hydroxyl-group, especially preferred at least two free hydroxy groups that are directly aromatically coupled, wherein it is especially preferred if at least two free hydroxy-groups are coupled directly to an aromatic ring, and more especially preferred, positioned relative to each other in meta position. It is preferred that the aromatic alcohols are selected from phenols, cresoles (o-, m-, and p-cresol), naphthols (alpha and beta-naphthol) and thymol, as well as ethylphenols, propylphenols, fluoiphenols and methoxyphenols.

In one aspect, said polyurea based wall material may comprise a polyisocyanate. In some embodiments, the polyisocyanate is an aromatic polyisocyanate containing a phenyl, a toluoyl, xylyl, a naphthyl or a diphenyl moiety (e.g., a polyisocyanurate of toluene diisocyanate, trimethylol propane-adduct of toluene diisocyanate or a trimethylol propane-adduct of xylylene diisocyanate), an aliphatic polyisocyanate (e.g., a trimer of hexamethylene diisocyanate, a trimer of isophorone diisocyanate and a biuret of hexamethylene diisocyanate), or a mixture thereof (e.g., a mixture of a biuret of hexamethylene diisocyanate and a trimethylol propane-adduct of xylylene diisocyanate). In still other embodiments, the polyisocyanate may be cross-linked, the cross-linking agent being a polyamine (e.g., diethylenetriamine, bis(3-aminopropyl)amine, bis(hexanethylene)triamine, tris(2-aminoethyl)amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, dimethylbiguanide hydrochloride, or guanidine carbonate).

In one aspect, said polyvinyl alcohol based wall material may comprise a crosslinked, hydrophobically modified polyvinyl alcohol, which comprises a crosslinking agent comprising i) a first dextran aldehyde having a molecular weight of from 2,000 to 50,000 Da; and ii) a second dextran aldehyde having a molecular weight of from greater than 50,000 to 2,000,000 Da.

In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. Suitable deposition aids are described above and in the section titled "Deposition Aid". In one aspect, the microcapsule may be a perfume microcapsule. In one aspect, one or more types of microcapsules, for examples two microcapsules types, wherein one of the first or second microcapsules (a) has a wall made of a different wall material than the other; (b) has a wall that includes a different amount of wall material or monomer than the other; or (c) contains a different amount perfume oil ingredient than the other; or (d) contains a different perfume oil, may be used.

In one aspect, said perfume delivery technology may comprise an amine compound (ARP) or a thio compound. One may also use "reactive" polymeric amines and or polymeric thios in which the amine and/or thio functionality is pre-reacted with one or more PRMs to form a compound. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release.

Dye Transfer Inhibiting Agents

Fabric cleaning compositions may also include one or more materials effective for inhibiting the transfer of dyes from one fabric to another during the cleaning process. Generally, such dye transfer inhibiting agents may include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents may be used at a concentration of about 0.0001% to about 10%, by weight of the composition, in some examples, from about 0.01% to about 5%, by weight of the composition, and in other examples, from about 0.05% to about 2% by weight of the composition.

Chelating Agents

The detergent compositions described herein may also contain one or more metal ion chelating agents. Suitable molecules include copper, iron and/or manganese chelating agents and mixtures thereof. Such chelating agents can be selected from the group consisting of phosphonates, amino carboxylates, amino phosphonates, succinates, polyfunctionally-substituted aromatic chelating agents, 2-pyridinol-N-oxide compounds, hydroxamic acids, carboxymethyl insulins and mixtures thereof. Chelating agents can be present in the acid or salt form including alkali metal, ammonium, and substituted ammonium salts thereof, and mixtures thereof.

Aminocarboxylates useful as chelating agents include, but are not limited to ethylenediaminetetracetates (EDTA); N-(hydroxyethyl)ethylenediaminetriacetates (HEDTA); nitrilotriacetates (NTA); ethylenediamine tetraproprionates; triethylenetetraaminehexacetates, diethylenetriamine-pentaacetates (DTPA); methylglycinediacetic acid (MGDA); Glutamic acid diacetic acid (GLDA); ethanoldiglycines; triethylenetetraaminehexaacetic acid (TTHA); N-hydroxyethyliminodiacetic acid (HEIDA); dihydroxyethylglycine (DHEG); ethylenediaminetetrapropionic acid (EDTP) and derivatives thereof.

Phosphorus containing chelants include, but are not limited to diethylene triamine penta (methylene phosphonic acid) (DTPMP CAS 15827-60-8); ethylene diamine tetra (methylene phosphonic acid) (EDTMP CAS 1429-50-1); 2-Phosphonobutane 1,2,4-tricarboxylic acid (Bayhibit® AM); hexamethylene diamine tetra(methylene phosphonic acid) (CAS 56744-47-9); hydroxy-ethane diphosphonic acid (HEDP CAS 2809-21-4); hydroxyethane dimethylene phosphonic acid; 2-phosphono-1,2,4-Butanetricarboxylic acid (CAS 37971-36-1); 2-hydroxy-2-phosphono-Acetic acid (CAS 23783-26-8); Aminotri(methylenephosphonic acid) (ATMP CAS 6419-19-8); P,P'-(1,2-ethanediyl)bis-Phosphonic acid (CAS 6145-31-9); P,P'-methylenebis-Phosphonic acid (CAS 1984-15-2); Triethylenediaminetetra(methylene phosphonic acid) (CAS 28444-52-2); P-(1-hydroxy-1-methylethyl)-Phosphonic acid (CAS 4167-10-6); bis(hexamethylene triamine penta(methylenephosphonic acid)) (CAS 34690-00-1); N2,N2,N6,N6-tetrakis(phosphonomethyl)-Lysine (CAS 194933-56-7, CAS 172780-03-9), salts thereof, and mixtures thereof. Preferably, these aminophosphonates do not contain alkyl or alkenyl groups with more than about 6 carbon atoms.

A biodegradable chelator that may also be used herein is ethylenediamine disuccinate ("EDDS"). In some examples, but of course not limited to this particular example, the [S,S] isomer. In other examples, the trisodium salt of EDDA may be used, though other forms, such as magnesium salts, may also be useful. Polymeric chelants such as Trilon P® from BASF may also be useful.

Polyfunctionally-substituted aromatic chelating agents may also be used in the cleaning compositions. Compounds of this type in acid form are dihydroxydisulfobenzenes, such as 1,2-dihydroxy-3,5-disulfobenzene, also known as Tiron. Other sulphonated catechols may also be used. In addition to the disulfonic acid, the term "tiron" may also include mono- or di-sulfonate salts of the acid, such as, for example, the disodium sulfonate salt, which shares the same core molecular structure with the disulfonic acid.

The detergent composition according to the present invention may comprise a substituted or unsubstituted 2-pyridinol-N-oxide compound or a salt thereof, as a chelating agent. Included within the scope of this invention are tautomers of this compound, e.g., 1-Hydroxy-2(1H)-pyridinone, as chelating agents. In certain aspects, the detergent composition comprises a 2-pyridinol-N-oxide compound selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof. In certain aspects, the detergent composition comprises a 1-Hydroxy-2(1H)-pyridinone compound selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid,methyl ester (CAS 36979-78-9); 1-hydroxy-5-nitro-2(1H)-Pyridinone (CAS 45939-70-6); and mixtures thereof. These compounds are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

Hydroxamic acids are a class of chemical compounds in which a hydroxylamine is inserted into a carboxylic acid and be used as chelating agents. The general structure of a hydroxamic acid is the following:

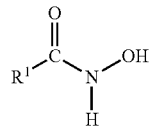

The preferred hydroxamates are those where $R^1$ is $C_4$ to $C_{14}$ alkyl, preferably normal alkyl, most preferably saturated, salts thereof and mixtures thereof. When the C8 material is used, it called octyl hydroxamic acid.

Other suitable chelating agents for use herein are the commercial DEQUEST series, and chelants from Monsanto, Akzo-Nobel, DuPont, Dow, the Trilon® series from BASF and Nalco.

The chelant may be present in the detergent compositions disclosed herein at from about 0.005% to about 15% by weight, about 0.01% to about 5% by weight, about 0.1% to about 3.0% by weight, or from about 0.2% to about 0.7% by weight, or from about 0.3% to about 0.6% by weight of the detergent compositions disclosed herein.

Hygiene and Malodour

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release $Ag^+$ or nano-silver dispersions.

Fillers and Carriers

Fillers and carriers may be used in the cleaning compositions described herein. As used herein, the terms "filler" and "carrier" have the same meaning and can be used interchangeably.

Liquid cleaning compositions and other forms of cleaning compositions that include a liquid component (such as liquid-containing unit dose cleaning compositions) may contain water and other solvents as fillers or carriers. Suitable solvents also include lipophilic fluids, including siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, and mixtures thereof.

Low molecular weight primary or secondary alcohols exemplified by methanol, ethanol, propanol, and isopropanol are suitable. Monohydric alcohols may be used in some examples for solubilizing surfactants, and polyols such as those containing from 2 to about 6 carbon atoms and from 2 to about 6 hydroxy groups (e.g., 1,3-propanediol, ethylene glycol, glycerine, and 1,2-propanediol) may also be used. Amine-containing solvents, such as monoethanolamine, diethanolamine and triethanolamine, may also be used.

The cleaning compositions may contain from about 5% to about 90%, and in some examples, from about 10% to about 50%, by weight of the composition, of such carriers. For compact or super-compact heavy duty liquid or other forms of cleaning compositions, the use of water may be lower than about 40% by weight of the composition, or lower than about 20%, or lower than about 5%, or less than about 4% free water, or less than about 3% free water, or less than about 2% free water, or substantially free of free water (i.e., anhydrous).

For powder or bar cleaning compositions, or forms that include a solid or powder component (such as powder-containing unit dose cleaning composition), suitable fillers may include, but are not limited to, sodium sulfate, sodium chloride, clay, or other inert solid ingredients. Fillers may also include biomass or decolorized biomass. Fillers in granular, bar, or other solid cleaning compositions may comprise less than about 80% by weight of the cleaning composition, and in some examples, less than about 50% by weight of the cleaning composition. Compact or supercompact powder or solid cleaning compositions may comprise less than about 40% filler by weight of the cleaning composition, or less than about 20%, or less than about 10%.

For either compacted or supercompacted liquid or powder cleaning compositions, or other forms, the level of liquid or solid filler in the product may be reduced, such that either the same amount of active chemistry is delivered to the wash liquor as compared to noncompacted cleaning compositions, or in some examples, the cleaning composition is more efficient such that less active chemistry is delivered to the wash liquor as compared to noncompacted compositions. For example, the wash liquor may be formed by contacting the cleaning composition to water in such an amount so that the concentration of cleaning composition in the wash liquor is from above 0 g/l to 6 g/l. In some examples, the concentration may be from about 0.5 g/l to about 5 g/l, or to about 3.0 g/l, or to about 2.5 g/l, or to about 2.0 g/l, or to about 1.5 g/l, or from about 0 g/l to about 1.0 g/l, or from about 0 g/l to about 0.5 g/l. These dosages are not intended to be limiting, and other dosages may be used that will be apparent to those of ordinary skill in the art.

Buffer System

The cleaning compositions described herein may be formulated such that, during use in aqueous cleaning operations, the wash water will have a pH of between about 7.0 and about 12, and in some examples, between about 7.0 and about 11. Techniques for controlling pH at recommended usage levels include the use of buffers, alkalis, or acids, and are well known to those skilled in the art. These include, but are not limited to, the use of sodium carbonate, citric acid or sodium citrate, lactic acid or lactate, monoethanol amine or other amines, boric acid or borates, and other pH-adjusting compounds well known in the art.

The cleaning compositions herein may comprise dynamic in-wash pH profiles. Such cleaning compositions may use wax-covered citric acid particles in conjunction with other pH control agents such that (i) about 3 minutes after contact with water, the pH of the wash liquor is greater than 10; (ii) about 10 minutes after contact with water, the pH of the wash liquor is less than 9.5; (iii) about 20 minutes after contact with water, the pH of the wash liquor is less than 9.0; and (iv) optionally, wherein the equilibrium pH of the wash liquor is in the range of from about 7.0 to about 8.5.

UV Absorbers—in certain consumer product embodiments of the present invention, the photo-responsive encapsulates of the present invention may be stabilized against premature release by exposure to light of a sufficient wavelength during storage by incorporation of a suitable UV-absorbing ingredients into the composition. Any suitable UV-absorbing composition may be employed, but particularly preferred are those which do not impart an unpleasant color or odor to the composition, and which do not adversely affect the rheology of the product. Non-limiting examples of UV-absorbing ingredients include avobenzone, cinoxate, ecamsule, menthyl anthranilate, octyl methoxycinnamate, octyl salicylate, oxybenzone, sulisobenzone, and combinations thereof. Applicants have surprisingly found that the use of such UV-absorbing ingredients do not compromise the light-activated performance of encapsulates of the present invention. Without wishing to be bound by theory, it is believed that in many consumer product applications, e.g., cleaning compositions including laundry detergents, shampoos and body washes, the UV absorbing ingredient is washed down the drain while the encapsulates of the present invention are retained in an efficacious amount on the surface of interest where they are available to release their contents on subsequent exposure to light of a sufficient wavelength. In other cleaning compositions or leave-on consumer products, e.g., floor cleaning compositions, drapery and upholstery refreshers, body lotions, and hair styling products, it is believed that the UV-absorbing ingredients dry down to a thin film after application, allowing the encapsulates of the present invention to sit atop or extend above the film. This allows and efficacious amount of light of the desired wavelength to reach the encapsulates and effect the release of the benefit agents.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

An aminoester terminated polydimethylsiloxane is produced as follows:

A carboxypropyl terminated polydimethylsiloxane, DMS-B31 (25.00 g; 28,000 MW; Available from Gelest, Inc., Morrisville, Pa.) is combined with N,N-dimethylethanolamine (0.64 g;

Available from Sigma-Aldrich, St. Louis, Mo.). The mixture is heated while stirring for 16 hours at 180° C. with removal of water, after which the mixture is placed under reduced pressure to remove excess N,N-dimethylethanolamine. The reaction product is analyzed via $^1$H NMR and contains the ester functionality.

Example 2

An amino/methacryloyloxy Michael Adduct terminated polydimethylsiloxane is produced as follows:

A methacryloyloxypropyl terminated polydimethylsiloxane, DMS-R31 (95.00 g; 25,000 MW;

Available from Gelest, Inc., Morrisville, Pa.) is combined with ethylenediamine (3.65 g;

Available from Sigma-Aldrich, St. Louis, Mo.) and 2-ethyl-1-hexanol (24.21 g; Available from Sigma-Aldrich, St. Louis, Mo.). The mixture is heated while stirring for 16 hours at 135° C., after which the mixture is placed under reduced pressure to remove excess ethylenediamine. The reaction product is analyzed via $^1$H NMR and contains the amino/methacryloyloxy Michael Adduct functionality.

Example 3

An aminoester terminated polydimethylsiloxane is produced as follows:

A carbinol (hydroxy) terminated polydimethylsiloxane, DMS-C23 (100.00 g; 10,000 MW;

Available from Gelest, Inc., Morrisville, Pa.) is combined with beta-alanine (7.13 g; Available from Sigma-Aldrich, St. Louis, Mo.). The mixture is heated while stirring for 16 hours at 180° C. with removal of water. The reaction product is analyzed via $^1$H NMR and contains the ester functionality.

Example 4

An aminoester terminated polydimethylsiloxane is produced as follows:

A carbinol (hydroxy) terminated polydimethylsiloxane, DMS-C23 (100.00 g; 10,000 MW;

Available from (iciest, Inc., Morrisville, Pa.) is combined with N,N-dimethyl-β-alanine (9.37 g; Available from Sigma-Aldrich, St. Louis, Mo.). The mixture is heated while stirring for 16 hours at 180° C. with removal of water, after which the mixture is placed under reduced pressure to remove excess N,N-dimethyl-β-alanine. The reaction product is analyzed via $^1$H NMR and contains the ester functionality.

Example 5

An amino/methacryloyloxy Michael Adduct side chain polydimethylsiloxane is produced as follows:

A (methacryloxypropyl)methylsiloxane-dimethylsiloxane copolymer, RMS-033 (5.00 g; 2600 Functional Group MW; Available from Gelest, Inc., Morrisville, Pa.) is combined with ethylenediamine (0.47 g; Available from Sigma-Aldrich, St. Louis, Mo.) and 2-ethyl-1-hexanol (1.37 g; Available from Sigma-Aldrich, St. Louis, Mo.). The mixture is heated while stirring for 16 hours at 135° C., after which the mixture is placed under reduced pressure to remove excess ethylenediamine. The reaction product is analyzed via $^1$H NMR and contains the amino/methacryloyloxy Michael Adduct functionality.

Example 6

An aminoester side chain polydimethylsiloxane is produced as follows:

A carbinol (hydroxy) side chain polydimethylsiloxane, CMS-222 (100.00 g; 2000 Functional Group MW; Available from Gelest, Inc., Morrisville, Pa.) is combined with N,N-dimethyl-β-alanine (23.43 g; Available from Sigma-Aldrich, St. Louis, Mo.). The mixture is heated while stirring for 16 hours at 180° C. with removal of water, after which the mixture is placed under reduced pressure to remove excess N,N-dimethyl-β-alanine. The reaction product is analyzed via $^1$H NMR and contains the ester functionality.

Example 7

An aminoester side chain polydimethylsiloxane is produced as follows:

A carbinol (hydroxy) side chain polydimethylsiloxane, CMS-222 (100.00 g; 2000 Functional Group MW; Available from Gelest, Inc., Morrisville, Pa.) is combined with beta-alanine (17.82 g; Available from Sigma-Aldrich, St. Louis, Mo.). The mixture is heated while stirring for 16 hours at 180° C. with removal of water. The reaction product is analyzed via $^1$H NMR and contains the ester functionality.

Example 8

An aminoester terminated polydimethylsiloxane is produced as follows:

A carboxydecyl terminated polydimethylsiloxane, DMS-B12 (25.00 g; 1000 MW; Available from Gelest, Inc., Morrisville, Pa.) is combined with N,N-dimethylethanolamine (17.83 g;

Available from Sigma-Aldrich, St. Louis, Mo.). The mixture is heated while stirring for 16 hours at 180° C. with liberation of water, after which the mixture is placed under reduced pressure to remove excess N,N-dimethylethanolamine. The reaction product is analyzed via $^1$H NMR and contains the ester functionality.

Example 9

An (Aminoester)methylsiloxane-Dimethylsiloxane copolymer is produced as follows:

A (Carboxydecyl)methylsiloxane-Dimethylsiloxane copolymer, (25.00 g; 488 g/mol carboxy equivalence) is combined with N,N-dimethylethanolamine (18.27 g; Available from Sigma-Aldrich, St. Louis, Mo.). The mixture is heated while stirring for 16 hours at 180° C. with liberation of water, after which the mixture is placed under reduced pressure to remove excess N,N-dimethylethanolamine. The reaction product is analyzed via $^1$H NMR and contains the ester functionality.

Example 10—Non-Limiting Examples of Product Formulations Containing a Silicone Compound are Summarized in the Following Table

| (% wt) | EXAMPLES | | | | | | | | | |
|---|---|---|---|---|---|---|---|---|---|---|
| | A | B | C | D | E | F | G | H | I | J |
| FSA [a] | 14 | 16.47 | 14 | 12 | 12 | 16.47 | — | — | 5 | 5 |
| FSA [b] | | | | | — | | 3.00 | — | — | — |
| FSA [c] | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Silicone compound according to Examples 1-9 | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |

-continued

| (% wt) | EXAMPLES | | | | | | | | | |
|---|---|---|---|---|---|---|---|---|---|---|
| | A | B | C | D | E | F | G | H | I | J |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i, j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Perfume | 0.8 | 0.7 | 0.9 | 0.5 | 1.2 | 0.5 | 1.1 | 0.6 | 1.0 | 0.9 |
| Deionized Water | * | * | * | * | * | * | * | * | * | * |

* Balance
[a] N,N-di(tallowoyloxyethyl)-N,N-dimethylammonium chloride.
[b] Methyl bis(tallow amidoethyl)2-hydroxyethyl ammonium methyl sulfate.
[c] Compound of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculan 44.

Example 11—Silicone Compounds in Dry Laundry Formulations

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroxyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |

| Component | % w/w granular laundry detergent composition | | | | | | |
|---|---|---|---|---|---|---|---|
| | A | B | C | D | E | F | G |
| Silicone compound according to Examples 1-9 | 1.3 | 2.4 | 1 | 1.3 | 1.3 | 1.3 | 0.7 |
| Balance Water * | * | * | * | * | * | * | * |

Example 12—Liquid Laundry Formulations (HDLs) Comprising Silicone Compounds

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Silicone compound according to Examples 1-9 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

Example 13

Examples of free flowing particles products that comprise silicone compound according to the present invention and/or microcapsule. The table below also exemplifies combinations which comprise also perfume free and in microcapsules or combinations of these with aforementioned combinations with malodor reduction materials and/or compositions. The table also exemplifies compositions having only malodor reduction materials and/or compositions free, in microcapsules and combinations thereof that have little to no fragrance to provide a product that is essentially 'fragrance free'

| | COMPOSITION | | | |
|---|---|---|---|---|
| | 1 | 2 | 3 | 4 |
| Component | % Wt Active | % Wt Active | % Wt Active | % Wt Active |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |

| Component | 1 % Wt Active | 2 % Wt Active | 3 % Wt Active | 4 % Wt Active |
|---|---|---|---|---|
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Free Perfume | 0-5 | 0-5 | 0-5 | 0-5 |
| Total Silicone compound according to Examples 1-9 and optional microcapsules | 0.001-10 | 0.001-4.5 | 0.001-3 | 0.001-7.5 |
| Balance Water* | * | * | * | * |

| | COMPOSITION | | | |
|---|---|---|---|---|
| Component | 5 % Wt Active | 6 % Wt Active | 7 % Wt Active | 8 % Wt Active |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Total Silicone compound according to Examples 1-9 and optional microcapsules | 0.001-10 | 0.001-4.5 | 0.001-3 | 0.001-7.5 |
| Balance Water* | * | * | * | * |

(1) PEG
(2) Clay
(3) Urea
(4) Polysaccharide, mostly starches, unmodified starches, starch derivatives, acid-modified starch and kappa carrageenan
(5) Zeolite
(6) Starch/Zeolite - SEA
(7) Metal oxides - non-limiting examples - TiO2, ZnO, MnO
(8) Metal catalysts
(9) Opacifier The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A silicone compound comprising a silicone moiety, a moiety comprising a functional group and a moiety comprising a cleavable bond, said moiety comprising said cleavable bond linking said silicone moiety and said moiety comprising said functional group,
wherein said silicone compound has the formula:

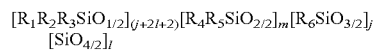

wherein:
a) j is an integer from 0 to 150;
b) m is an integer from 0 to 1500;
c) l is an integer from 0 to 150;
with the provisio j+m+l equals an integer greater than or equal to 1;
d) each of $R_1$, $R_2$, $R_3$, $R_4$, $R_5$ and $R_6$ moiety is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy, and —$X_t$-A-Y, where in index t is 0 or 1, with the provisio that at least one of the moieties $R_1$ through $R_6$═—$X_t$-A-Y;

(i) each X moiety is independently, an unsubstituted divalent alkylene radical comprising 1-24 carbon atoms;

(ii) each A moiety is independently selected from the group consisting of

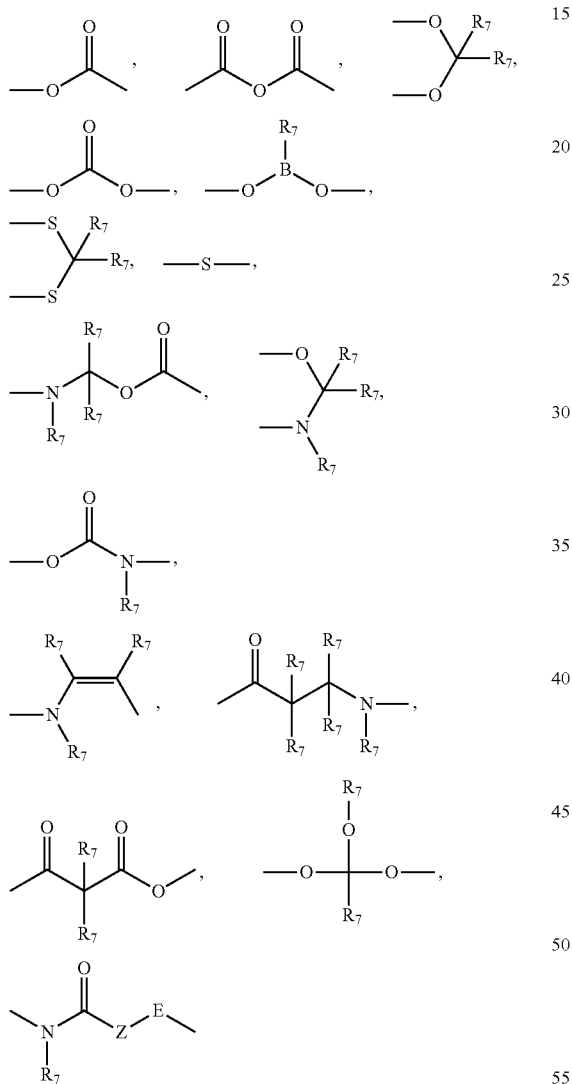

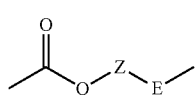

E=electron withdrawing group;

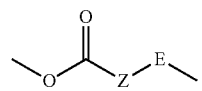

E=electron withdrawing group;

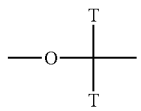

T wherein T is selected from an electron withdrawing group E or $R_7$, with the proviso that at least one T is E; each $R_7$ moiety for each A moiety is independently selected from the group consisting of H, $C_1$-$C_{32}$ alkyl, C1-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl; and each Z for each A moiety is independently selected from the group consisting of:

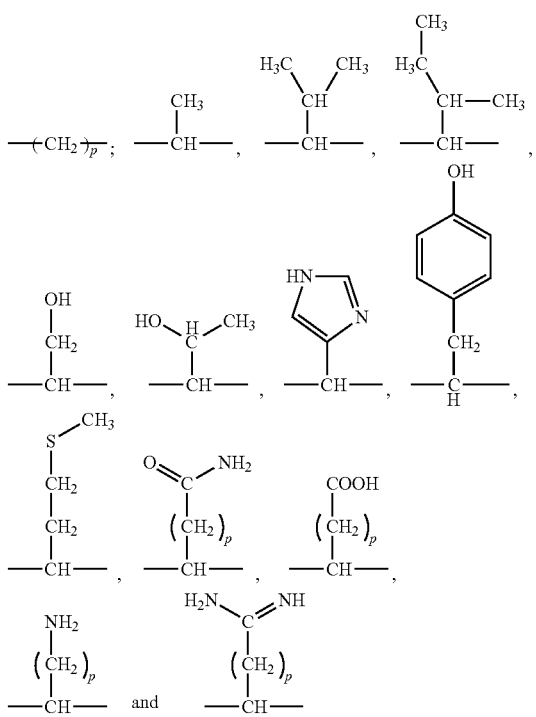

where p is an integer from 1-32;

(ii) each Y is independently selected from the group consisting of a $C_1$-$C_{32}$ alkyl, a $C_5$-$C_{32}$ aryl, and a $C_6$-$C_{32}$ alkylaryl comprising at least one substituent selected from the group consisting of an ether moiety, an alkene moiety, an alkyne moiety, an aldehyde moiety, a ketone moiety, an ester moiety, a carbonate moiety, an amide moiety, a nitrile moiety, a peroxide moiety, an acetal moiety, a hemiacetal moiety, a hemiketal moiety, a ketal moiety, an orthoester moiety, orthocarbonate ester, an imine moiety, an imide moiety, an azide moiety, an azo moiety, a cyanate moiety, a nitrate moiety, a nitrite moiety, a nitro moiety, a nitroso moiety, an oxime, a sulfide moiety, a disulfide moiety, a sulfoxide moiety, a sulfone moiety, a sulfinic acid moiety, a sulfonic acid moiety, a thiocyanate moiety, a thione moiety, a thial moiety, a phosphine moiety, a phosphonic acid moiety, a phosphate moiety, a phosphodiester moiety, a boronic acid moiety, a boronic ester moiety, a borinic acid moiety, a borinic ester moiety, an amino moiety, an epoxy moiety, an alkoxy moiety, a hydroxy moiety, a thiol moiety, a halide moiety, an oxyalkylene moiety, an anhydride moiety, a carboxy moiety, a silane moiety, a siloxane moiety and a quaternary ammonium moiety.

2. A silicone compound according to claim 1 wherein each A moiety is independently selected from the group consisting of

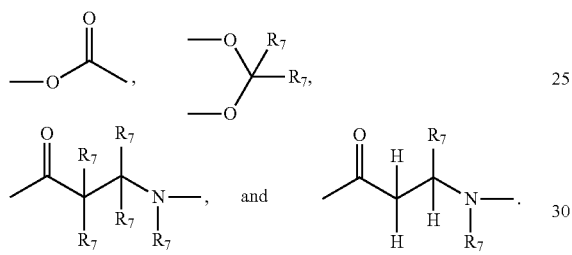

3. A silicone compound according to claim 1 wherein each Y moiety is independently selected from the group consisting of

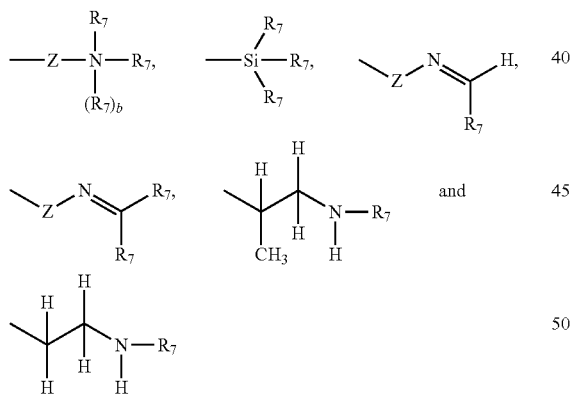

wherein b is 0 or 1 with the proviso that when b=1 then, the positive charge on the nitrogen is balanced by a suitable anion.

4. A silicone compound according to claim 1 wherein each A-Y moiety is independently selected from the group consisting of:

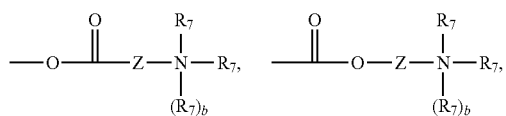

wherein b is 0 or 1 with the proviso that when b=1 the positive charge on the nitrogen is balanced by a suitable anion and each Z for each A-Y moiety is independently selected from the group consisting of:

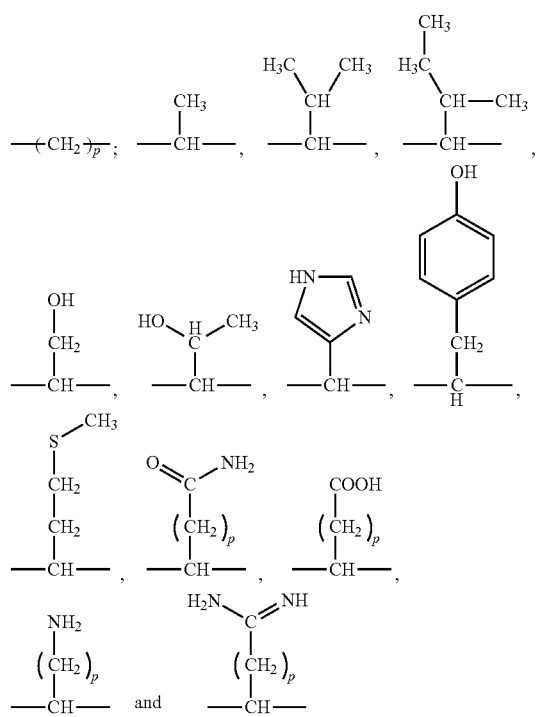

where p is an integer from 1-32.

5. A consumer product composition comprising:
a.) from about 0.001% to about 10% of a silicone compound according to claim 1, and
b.) a consumer product ingredient.

6. A consumer product according to claim 5, consumer product being a cleaning and/or treatment composition.

7. A cleaning and/or treatment composition according to claim 6 comprising a consumer product ingredient selected from the group consisting of surfactants, color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume, an additional perfume delivery system, structure elasticizing agents, thickeners/structurants, fabric softeners, carriers, hydrotropes, oligoamines, processing aids, hueing agents, pigments and mixtures thereof.

8. A consumer product comprising a silicone compound according to claim 1 packaging, said silicone compound being attached or adhered to said packaging.

9. A method of treating and/or cleaning a situs, said method comprising
   a.) optionally washing and/or rinsing said situs;
   b.) contacting said situs with a silicone compound according to claim 1; and
   c.) optionally washing and/or rinsing said situs.

10. A situs treated with a silicone compound according to claim 1.

11. A consumer product according to claim 5, wherein the silicone compound comprises at least one Y group selected from the group consisting of: an amide moiety, a nitrile moiety, an imine moiety, an imide moiety, an azide moiety, an azo moiety, a cyanate moiety, a nitrate moiety, a nitrite moiety, a nitro moiety, a nitroso moiety, an oxime, an amino moiety, and a quaternary ammonium moiety.

12. A consumer product according to claim 5, wherein the silicone compound comprises at least one Y group that is an amine moiety.

13. A consumer product according to claim 5, wherein the silicone compound comprises at least one Y group that is an imide moiety.

14. A consumer product according to claim 5, wherein the silicone compound comprises at least one Y group that is an amino moiety.

15. A consumer product according to claim 5, wherein the silicone compound comprises at least one Y group that is a quaternary ammonium moiety.

16. A consumer product according to claim 5, wherein each A moiety of the silicone compound is

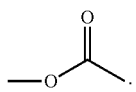

17. A consumer product according to claim 11, wherein each A moiety of the silicone compound is

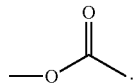

18. A consumer product according to claim 1, wherein each Y group independently comprises at least one substituent selected from the group

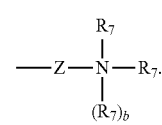

19. A consumer product according to claim 1, wherein each Y group independently comprises at least one substituent selected from the group

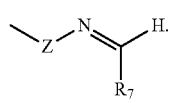

20. A consumer product according to claim 1, wherein each Y group independently comprises at least one substituent selected from the group

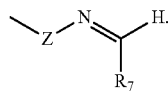

* * * * *